United States Patent
Li et al.

(10) Patent No.: US 11,120,584 B2
(45) Date of Patent: Sep. 14, 2021

(54) SYSTEM AND METHOD FOR REMOVING GIBBS ARTIFACT IN MEDICAL IMAGING SYSTEM

(71) Applicant: SHANGHAI UNITED IMAGING INTELLIGENCE CO., LTD., Shanghai (CN)

(72) Inventors: Guobin Li, Shanghai (CN); Nan Liu, Shanghai (CN); Xiaoqian Huang, Shanghai (CN); Shu Liao, Shanghai (CN)

(73) Assignee: SHANGHAI UNITED IMAGING INTELLIGENCE CO., LTD., Shanghai (CN)

(*) Notice: Subject to any disclaimer, the term of this patent is extended or adjusted under 35 U.S.C. 154(b) by 208 days.

(21) Appl. No.: 16/257,769

(22) Filed: Jan. 25, 2019

(65) Prior Publication Data
US 2019/0244399 A1 Aug. 8, 2019

Related U.S. Application Data

(63) Continuation-in-part of application No. 15/314,058, filed as application No. PCT/CN2016/084024 on May 31, 2016, now Pat. No. 10,203,393.

(30) Foreign Application Priority Data

Jan. 16, 2019 (CN) .......................... 201910041510.6

(51) Int. Cl.
G06K 9/00 (2006.01)
G06T 11/00 (2006.01)
(Continued)

(52) U.S. Cl.
CPC .......... G06T 11/008 (2013.01); A61B 5/055 (2013.01); A61B 5/7257 (2013.01);
(Continued)

(58) Field of Classification Search
CPC .............. G01R 33/4824; G01R 33/561; G01R 33/5611; G01R 33/56308;
(Continued)

(56) References Cited

U.S. PATENT DOCUMENTS 5,546,472 A * 8/1996 Levin ................. G01R 33/5608
382/131
7,450,779 B2 * 11/2008 Ferrari ..................... G06K 9/40
382/128
(Continued)

FOREIGN PATENT DOCUMENTS

CN 104013403 A 9/2014
CN 104156994 A 11/2014
(Continued)

OTHER PUBLICATIONS

Wang, Yida, et al. "Reduction of Gibbs artifacts in magnetic resonance imaging based on Convolutional Neural Network." 2017 10th international congress on image and signal processing, biomedical engineering and informatics (CISP-BMEI). IEEE, 2017. (Year: 2017).*

(Continued)

*Primary Examiner* — Avinash Yentrapati
(74) *Attorney, Agent, or Firm* — Metis IP LLC

(57) ABSTRACT

The present disclosure is related to systems and methods for image processing. The method may include obtaining a first set of image data. The method may also include generating a second set of image data by processing, based on a trained machine learning model, the first set of image data. The second set of image data may have a relatively high resolution and/or a relatively low level of artifacts with respect to the first set of image data. The method may further include
(Continued)

generating a target image by performing a weighted fusion on the first set of image data and the second set of image data.

20 Claims, 9 Drawing Sheets

(51) Int. Cl.
*G01R 33/565* (2006.01)
*A61B 5/055* (2006.01)
*G01R 33/561* (2006.01)
*G06T 5/00* (2006.01)
*A61B 5/00* (2006.01)
*G06T 5/50* (2006.01)
*G01R 33/56* (2006.01)

(52) U.S. Cl.
CPC ........ *A61B 5/7267* (2013.01); *G01R 33/5611* (2013.01); *G01R 33/56509* (2013.01); *G01R 33/56545* (2013.01); *G06T 5/002* (2013.01); *G06T 5/50* (2013.01); *G06T 11/006* (2013.01); *A61B 2576/00* (2013.01); *G01R 33/5608* (2013.01); *G06T 2207/10088* (2013.01); *G06T 2207/20081* (2013.01); *G06T 2207/20221* (2013.01)

(58) Field of Classification Search
CPC ........ G01R 33/56366; G01R 33/56509; G06T 11/006; G06T 11/008; G06T 2211/424; G06T 2211/428; G06T 5/002
See application file for complete search history.

(56) References Cited

U.S. PATENT DOCUMENTS

| | | | |
|---|---|---|---|
| 8,553,964 | B2 | 10/2013 | Chefd'hotel et al. |
| 9,208,588 | B2* | 12/2015 | Chen ........................ G06T 5/002 |
| 10,635,943 | B1* | 4/2020 | Lebel ........................ G06T 5/50 |
| 2004/0113403 | A1 | 6/2004 | Mills et al. |
| 2004/0113614 | A1* | 6/2004 | Liang .................. G01R 33/561 324/307 |
| 2008/0012562 | A1* | 1/2008 | Beatty ................ G01R 33/5611 324/307 |
| 2010/0034447 | A1* | 2/2010 | Geier .................. G01R 33/482 382/131 |
| 2012/0148128 | A1* | 6/2012 | Chefd'hotel ..... G01R 33/56509 382/131 |
| 2015/0086097 | A1* | 3/2015 | Chen .................... G06T 11/008 382/131 |
| 2015/0187072 | A1* | 7/2015 | Zhai .................. G01R 33/5608 382/131 |
| 2015/0192653 | A1* | 7/2015 | Sharif .............. G01R 33/56366 600/420 |
| 2015/0279065 | A1* | 10/2015 | Li ...................... G01R 33/5611 382/131 |
| 2015/0369893 | A1* | 12/2015 | Takeshima ....... G01R 33/56545 324/309 |
| 2016/0003928 | A1* | 1/2016 | Chen .................. G01R 33/4822 324/309 |
| 2017/0071562 | A1* | 3/2017 | Suzuki .................... A61B 6/025 |
| 2018/0144466 | A1* | 5/2018 | Hsieh .................... G06T 7/0012 |
| 2019/0004132 | A1* | 1/2019 | Tan .................... G01R 33/4818 |
| 2019/0209867 | A1* | 7/2019 | Sun ........................ G06K 9/3233 |
| 2019/0257905 | A1* | 8/2019 | Cheng ................ G01R 33/5611 |
| 2020/0126190 | A1* | 4/2020 | Lebel ........................ G06K 9/66 |

FOREIGN PATENT DOCUMENTS

| | | |
|---|---|---|
| CN | 104392473 A | 3/2015 |
| CN | 104714200 A | 6/2015 |

OTHER PUBLICATIONS

International Search Report in PCT/CN2016/084024 dated Feb. 21, 2017, 4 pages.
Written Opinion in PCT/CN2016/084024 dated Feb. 21, 2017, 4 pages.
Lustig M. et al. Sparse MRI: The Application of Compressed Sensing for Rapid MR Imaging, Magnetic Resonance in Medicine, 2007, 58:1182-1195, 14 pages.
Block K. T. et al. Suppression of MRI Truncation Artifacts Using Total Variation Constrained Data Extrapolation. International Journal of Biomedical Imaging, 2008, Article ID 184123, 8 pages.
Ya Wang. A New Method of MRI Image Reconstruction Based on All Phase FFT. China Dissertation Database 03, 2015, pp. 19-21, 7 pages.
Si Ye et al. Study on Restraining Truncation Artifacts in MRI Based on Total Variation Denoising. Computer Application and Software, 2013, 3:268-270, 3 pages.
Krissian et al. "Noise-Driven Anisotropic Diffusion Filtering of MRI", 2009, 10 pages.
Nencka et al. "A Mathematical Model for Understanding the Statistical effects of k-space (AMMUST-k) preprocessing on observed voxel measurements in fcMRI and fMRI" 2009, 15 pages.
First Office Action in Chinese Application No. 201680086270.6 dated May 29, 2020, 13 pages.
Ye, Si, The study of truncation artifacts reduction in MR image based on total variation denoising, China Dissertation Database, 2013, 85 pages.
The Extended European Search Report in European Application No. 16815528.1 dated Jan. 14, 2020, 9 pages.
Jelle Veraart et al., Gibbs Ringing in Diffusion MRI, Magnetic Resonance in Medicine, 76(1): 301-314, 2015.
Kai Tobias Block et al., Suppression of MRI Truncation Artifacts Using Total Variation Constrained Data Extrapolation, International Journal of Biomedical Imaging, pp. 1-8, 2008.
Zha L.et al., A Simple Fast Method of Gibbs Ringing Artifact and Noise Reduction with Edge Enhancement Using Low-pass, Band-pass, and High-pass K-Space Windowing Functions, Proceedings of the International Society for Magnetic Resonance in Medicine, p. 2702, 2011.

* cited by examiner

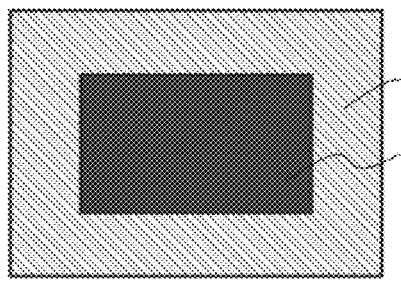
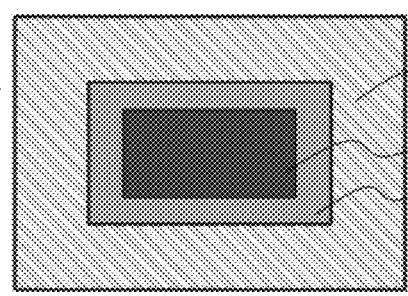
FIG. 10A    FIG. 10B
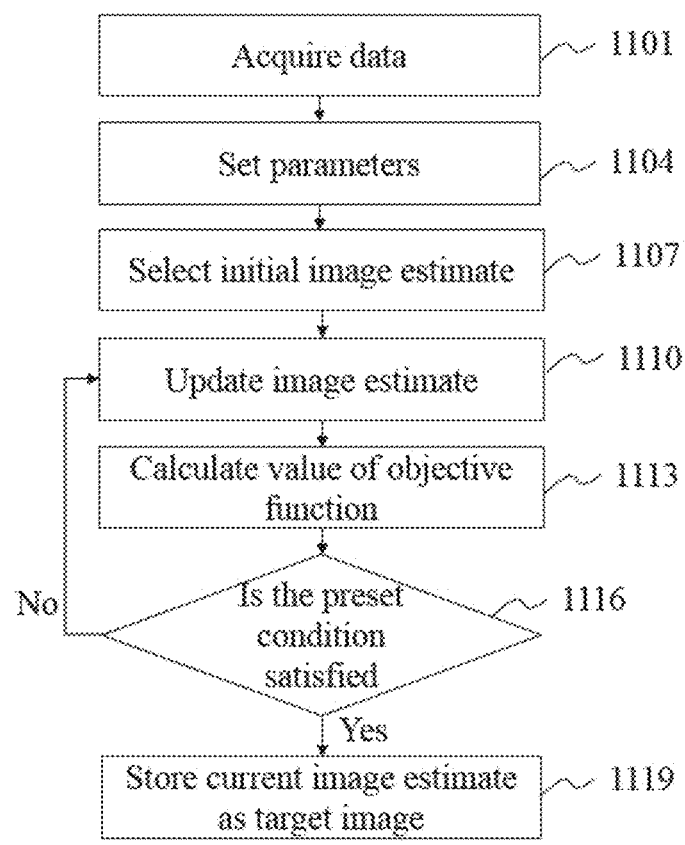
FIG. 11A

SYSTEM AND METHOD FOR REMOVING GIBBS ARTIFACT IN MEDICAL IMAGING SYSTEM

CROSS-REFERENCE TO RELATED APPLICATIONS

This present application claims priority of Chinese Patent Application No. 201910041510.6 filed on Jan. 16, 2019, and is a continuation in part of U.S. application Ser. No. 15/314,058, filed on Nov. 25, 2016, which is a U.S. national stage under 35 U.S.C. § 371 of International Application No. PCT/CN2016/084024, filed on May 31, 2016, designating the United States of America, the contents of each of which are hereby incorporated by reference.

TECHNICAL FIELD

The present disclosure generally relates to a system and method for image processing, and more particularly, a system and method for improving quality of a reconstructed image.

BACKGROUND

An image taken by an imaging system, such as a magnetic resonance imaging (MRI) system, may be represented either as an image data in the space domain or as an image-related data in the k-space, i.e. the frequency domain. Sharp transitions in the image, such as those near the boundary of an organ, may be demonstrated in the k-space using relatively high frequency components. Nevertheless, the limited time of sampling or poor signal to noise (SNR) ratio may lead to the under-sampling of image data in the k-space. It may result in the shortage of high-frequency components in the image data, thus causing the phenomenon of "ringing" in the reconstructed image. It is often referred to as the "Gibbs artifact."

Accordingly, it would be desirable to effectively and substantially reduce the ringing artifact in the reconstructed image while substantially maintaining the resolution and the signal-to-noise ratio of the final image without increasing the scan time.

SUMMARY

The present disclosure relates to image processing. Specifically, one aspect of the present disclosure relates to a method for reducing the Gibbs artifact and/or the effect of under-sampling of k-space data in the reconstructed image. According to some embodiments of the present disclosure, the method may be based on undersampled image-related data in the k-space. Specifically, the method may include filling a matrix of sampled data in the k-space. Some procedure of pre-processing, such as filtering and padding, may be performed first. For example, a low-pass filter may be applied on the matrix of sampled data to attenuate the high-frequency component in the matrix of data. Besides the matrix of sampled data in the k-space, the matrix of sampled data may be extended to an outer area enclosing the matrix of data in the k-space, on which a padding may be performed. The padding may be a zero-padding or a non-zero padding.

Another aspect of the present disclosure relates to a non-transitory computer readable medium including executable instructions. The instructions, when executed by at least one processor, may cause the at least one processor to effectuate a method for image processing. In some embodiments, the non-transitory computer readable medium may include instructions for causing a computer to implement the method.

A further aspect of the present disclosure relates to a system for image processing. The system may include a frequency setting block to specify a first part and a second part of k-space. In some embodiments, the first part may include a first region and a second region. In some embodiments, the second part may be outside of the first part. The system may further include a storage block configured to fill a matrix comprising data in the first part of the k-space. The system may further include a filter configured to act on the matrix in the first part to produce a filtered data matrix in the first part. The system may further include a padding block to fill the second part of the k-space. The system may further include a calculation block to perform, based on a constraint, a plurality of iterations of an objective function for a target array comprising data in image domain, wherein the objective function is based on a total variation of the target array. The system may further include an image construction block to reconstruct an image based on the target array of data.

In some embodiments, the method may include one or more of the following operations. The k-space comprising a first part and a second part may be set. A matrix comprising data may be filled in the first part of the k-space. A filter may be applied on the matrix in the first part to produce a filtered data matrix in the first part. The second part of the k-space may be padded. A plurality of iterations of an objective function for a target array comprising data in image domain may be performed based on a constraint, wherein the objective function is based on a total variation of the target array. An image may be reconstructed based on the target array of data.

In some embodiments, the objective function may be based on a first function based on the Fourier transform of the target array, the filtered data matrix in the first part, and the padded data in the second part of the k-space.

In some embodiments, the matrix comprising data may be undersampled.

In some embodiments, the second part may be outside of the first part.

In some embodiments, the filter may be based on multiple orthogonal filters.

In some embodiments, the padding may be zero padding.

In some embodiments, the total variation may be based on a first order derivative of the target array of data in image domain.

In some embodiments, the total variation may be based on a second order derivative of the target array of data in image domain.

In some embodiments, the first part may be divided into a first region and a second region.

In some embodiments, the constraint may be given by setting the filtered data in the second region of the first part of the k-space to be invariant.

In some embodiments, the first function may be based on an L-2 norm function.

In some embodiments, the constraint may be given as a term of the objective function based on the Fourier transform of the target array and the filtered data in the second region of the first part of the k-space.

In some embodiments, the constraint may be based on an L-2 norm function.

In some embodiments, the constraint strength may be tuned by setting a coefficient for the term in the objective function.

According to another aspect of the present disclosure, a method implemented on a computing device may include a storage device and at least one processor for image processing. The method may include obtaining a first set of image data. The method may also include generating a second set of image data by processing, based on a trained machine learning model, the first set of image data. The second set of image data may have a relatively high resolution and/or a relatively low level of artifacts with respect to the first set of image data. The method may further include generating a target image by performing a weighted fusion on the first set of image data and the second set of image data.

In some embodiments, the method may also include obtaining the first set of image data based on k-space data generated by a magnetic resonance imaging (MRI) scanner.

In some embodiments, the k-space of the first set of image data may include a first part including the k-space center and a second part. The method may also include filling the first part of the k-space with k-space data generated by the MRI scanner. The method may further include padding the second part of the k-space with padded data.

In some embodiments, the method may also include obtaining the first set of image data by performing an inverse Fourier transform on the k-space data generated by the MRI scanner.

In some embodiments, the method may also include obtaining the first set of image data by collecting, using one or more reconstruction algorithms, the k-space data generated by the MRI scanner.

In some embodiments, the one or more image reconstruction algorithms may include at least one of a parallel imaging algorithm, a compressed sensing algorithm, a partial Fourier acquisition algorithm, or a regridding algorithm.

In some embodiments, the first set of image data may include a data array in k-space or a data array in an image domain.

In some embodiments, the second set of image data may include a data array in k-space or a data array in an image domain.

In some embodiments, the trained machine learning model may be obtained according to a process. The process may include obtaining a preliminary machine learning model. The process may also include obtaining a plurality of sets of input image data. The process may also include obtaining a plurality of sets of expected image data. The process may further include obtaining the trained machine learning model by training, based on the plurality of sets of input image data and the plurality of sets of expected image data, the preliminary machine learning model.

In some embodiments, the plurality of sets of input image data may include a plurality of data arrays in k-space or a plurality of data arrays in an image domain.

In some embodiments, the plurality of sets of expected image data may include a plurality of data arrays in k-space or a plurality of data arrays in an image domain.

In some embodiments, each set of input image data of the plurality of sets of input image data may correspond to a set of expected image data of the plurality of sets of expected image data. The each set of input image data may have a relatively low resolution and/or a relatively high level of artifacts with respect to the corresponding set of expected image data.

In some embodiments, the method may also include obtaining a first set of input image data based on k-space data generated by a magnetic resonance imaging (MRI) scanner.

In some embodiments, the method may also include reducing one or more artifacts in the first set of input image data by processing, based on one or more processing algorithms, the first set of input image data. The method may further include designating the first set of processed input image data as a first set of expected image data corresponding to the first set of input image data.

In some embodiments, the one or more artifacts may include a Gibbs artifact.

In some embodiments, the method may also include obtaining a second set of expected image data based on k-space data generated by a magnetic resonance imaging (MRI) scanner.

In some embodiments, the k-space of the second set of expected image data may include a first part and a second part. The method may also include obtaining a second set of input image data corresponding to the second set of expected image data by extracting a portion of the second set of expected image data in the first part of the k-space.

In some embodiments, the method may also include adjusting the second set of input image data by padding the second part of the k-space with padded data.

In some embodiments, the trained machine learning model may be a trained neural network model.

In some embodiments, the method may also include obtaining a first weight matrix corresponding to the first set of image data. The method may further include obtaining a second weight matrix corresponding to the second set of image data. The method may still further include generating the target image by performing, according to the first weight matrix and the second weight matrix, a weighted sum of the first set of image data and the second set of image data in k-space.

In some embodiments, the first weight matrix may include a first part and a second part. The first part may include the k-space center. The first part may include a first set of weighting factors. The second part may include a second set of weighting factors. Each of the first set of weighting factors may be larger than each of the second set of weighting factors. The second weight matrix may include a third part and a fourth part. The third part may include the k-space center. The third part may include a third set of weighting factors. The fourth part may include a fourth set of weighting factors. Each of the third set of weighting factors may be less than each of the fourth set of weighting factors.

In some embodiments, the method may also include filtering the first set of image data before processing, based on the trained machine learning model, the first set of image data or performing the weighted fusion.

According to another aspect of the present disclosure, a method implemented on a computing device may include a storage device and at least one processor for image processing. The method may include setting k-space including a first part and a second part. The method may also include obtaining a set of image data. The method may further include generating a target image by processing the set of image data based on a trained machine learning model. The trained machine learning model may be configured to process the set of image data to a less extent in the first part than the second part so that a changing extent of the set of image data in the first part may be less than a changing extent of the set of image data in the second part by the processing of the set of image data.

In some embodiments, the first part may include the k-space center.

In some embodiments, the trained machine learning model may be obtained according to a process. The process may include obtaining a preliminary machine learning model. The process may also include obtaining a plurality of sets of input image data. The process may also include obtaining a plurality of sets of expected image data. The process may further include obtaining the trained machine learning model by training the preliminary machine learning model based on the plurality of sets of input image data and the plurality of sets of expected image data. The preliminary machine learning model may be biased toward learning of characteristics of the plurality of sets of expected image data in the second part with respect to the first part during the training process.

In some embodiments, the first part may include a first region and a second region. The trained machine learning model may further be configured to setting a portion of the set of image data in the second region to be invariant during the processing.

In some embodiments, the second region may include the k-space center.

In some embodiments, the method may also include filtering the set of image data before processing, based on the trained machine learning model, the set of image data.

According to another aspect of the present disclosure, a system for image processing may include at least one storage device including a set of instructions or programs and at least one processor configured to communicate with the at least one storage device. When executing the set of instructions or programs, the at least one processor may be configured to cause the system to obtain a first set of image data. The at least one processor may also be configured to cause the system to generate a second set of image data by processing, based on a trained machine learning model, the first set of image data. The second set of image data may have a relatively high resolution and/or a relatively low level of artifacts with respect to the first set of image data. The at least one processor may further be configured to cause the system to generate a target image by performing a weighted fusion on the first set of image data and the second set of image data.

According to another aspect of the present disclosure, a system for image processing may include at least one storage device including a set of instructions or programs and at least one processor configured to communicate with the at least one storage device. When executing the set of instructions or programs, the at least one processor may be configured to cause the system to set k-space including a first part and a second part. The at least one processor may also be configured to cause the system to obtain a set of image data. The at least one processor may further be configured to cause the system to generate a target image by processing the set of image data based on a trained machine learning model. The trained machine learning model may be configured to process the set of image data to a less extent in the first part than the second part so that a changing extent of the set of image data in the first part is less than a changing extent of the set of image data in the second part by the processing of the set of image data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting examples, in which like reference numerals represent similar structures throughout the several views of the drawings, and wherein:

FIG. 10A shows an exemplary illustration of setting a larger region containing the natural region where the image-related data in the k-space occupy according to some embodiments of the present disclosure;

FIG. 10B shows an exemplary illustration of setting a larger region containing the natural region and setting a smaller region inside the natural region where the image-related data in the k-space occupy according to some embodiments of the present disclosure;

FIGS. 11A-11C illustrate exemplary flowcharts of a process for an image reconstruction according to some embodiments of the present disclosure;

DETAILED DESCRIPTION

Figure 1:
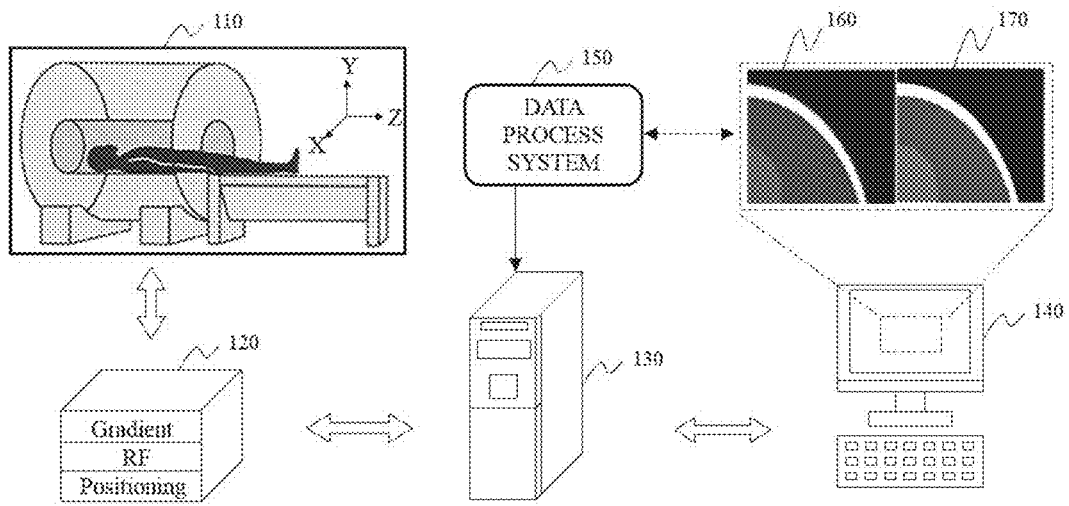
FIG. 1 illustrates an imaging system according to some embodiments of the present disclosure.

In the following detailed description, numerous specific details are set forth by way of example in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof. It will be further understood that the terms "constructed" and "reconstruct," when used in this disclosure, may represent a similar process that an image may be obtained based on image data.

In some embodiments, the present disclosure may be applicable to various modalities of imaging systems. Exemplary imaging modalities may include Digital Subtraction Angiography (DSA), Magnetic Resonance Imaging (MRI), Magnetic Resonance Angiography (MRA), Computed tomography (CT), Digital Radiography (DR), Computed Tomography Angiography (CTA), Ultrasound Scanning (US), Positron Emission Tomography (PET), Single-Photon Emission Computerized Tomography (SPECT), CT-MR, CT-PET, CE-SPECT, DSA-MR, PET-MR, PET-US, SPECT-US, TMS (transcranial magnetic stimulation)-MR, US-CT, US-MR, X-ray-CT, X-ray-MR, X-ray-portal, X-ray-US, Video-CT, Vide-US, or the like, or any combination thereof. This is understood that the following descriptions are provided in connection with medical image processing for illustration purposes and not intended to limit the scope of the present disclosure. The image processing disclosed herein may be used for purposes other than medical treatment or diagnosis. For instance, the image processing may be used for purposes of detecting a fracture within a structure or its progression over time, a non-uniform portion within a piece of material, etc.

In some embodiments, the subject may be a human being, an animal, an organ, a texture, a region, an object, a lesion, a tumor, or the like, or any combination thereof. Merely by way for example, the object may include a head, a breast, a lung, a trachea, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof. In some embodiments, the medical image may include a 2D image and/or a 3D image.

For illustration purposes, the following description is provided to help better understanding an image processing. It is understood that this is not intended to limit the scope of the present disclosure. For persons having ordinary skills in the art, a certain amount of variations, changes and/or modifications may be deducted under guidance of the present disclosure. However, those variations, changes and/or modifications do not depart from the scope of the present disclosure.

The present disclosure relates to image processing. Specifically, the present disclosure relates to a system and method for reducing the Gibbs artifact and/or the effect of under-sampling of k-space data in the reconstructed image. According to some embodiments of the present disclosure, the method may be based on undersampled image-related data in the k-space. The method may include performing iterations of an objective function. The objective function may be based on a total variation of a target array of data in the image domain. The objective function may be further based on a total variation of the target array of data and a function of the residual between the Fourier transform of the target array of data and the filtered image data being padded in the k-space. The iteration may be subject to a constraint given by, for example, setting the filtered image-related data in a region (e.g., an inner region) of the k-space to be invariant. The method may be based on undersampled data in the k-space. The method may provide an improved image with reduced Gibbs artifact and/or a reduced effect due to the under-sampling.

FIG. 1 illustrates an imaging system according to some embodiments of the present disclosure. The system may include an MRI (magnetic resonance imaging) scanner 110, a plurality of MRI auxiliary devices 120, a central controller 130, an input/output device 140, and a data processing system 150. The MRI scanner 110 may scan a subject located within it and generate a plurality of data relating to the subject. The MRI scanner 110 may include a main magnetic field generator, a plurality of gradient coils, a radiofrequency (RF) transmitter, and/or a RF receiver. The main magnetic field generator may generate a static magnetic field (for example, a magnetic field B0 in the Z direction). The main magnetic field generator may be of various types including, for example, a permanent magnet, a superconducting electromagnet, a resistive electromagnet, etc. The gradient coils may include X-gradient coils, Y-gradient coils, and Z-gradient coils. The gradient coils may generate magnetic field gradients to the main magnetic field in the X, Y, and/or Z directions to encode the spatial information of the subject being scanned. In some embodiments, the X-gradient is configured to provide the X-position information, which may be known as frequency encoding. In some embodiments, the Y-gradient is configured to provide the Y-position information, which may be known as phase encoding. The RF transmitter may include a plurality of RF coils. The RF transmitter may generate a RF magnetic field. Under the coordinated action of the static magnetic field, the gradient magnetic field and the RF magnetic field, MR signals relating to the subject being scanned may be generated. The RF receiver may receive the MR signals for image construction. The RF receiver may include a plurality of RF coils. In some embodiments, the function, size, type, geometry, position, amount, and/or magnitude of the main magnetic field generator, gradient coils, RF transmitter and receiver may be determined or changed according to one or more specific conditions. For example, according to the difference in function and size, the RF coils may be classified as volume coils and local coils. In some embodiments, the volume coils may include birdcage coils, transverse electromagnetic coils, surface coils, saddle coils, etc. In some embodiments, the local coils may include birdcage coils, solenoid coils, saddle coils, flexible coils, etc.

The MRI auxiliary devices 120 may coordinate with the MRI scanner 110 to generate a plurality of data relating to a subject. The MRI auxiliary devices 120 may include one or more gradient amplifiers, a RF amplifier, and a positioning device. The gradient amplifiers may be connected with the gradient coils in the MRI scanner 110. The gradient amplifiers may include an X gradient amplifier, a Y gradient amplifier, and a Z gradient amplifier. One or more of the gradient amplifiers may be connected to a waveform generator (not shown in FIG. 1). The waveform generator may generate various gradient waveforms that are applied to the gradient amplifiers. The waveforms (for example, currents or voltages) may be amplified by the gradient amplifiers and applied to the gradient coils to control the magnetic field strength and direction in the MRI scanner 110. The RF amplifier may be connected with the RF transmitter. The RF amplifier may be connected to a waveform generator (not shown in FIG. 1). The waveform generator may generate RF signals that are applied to the RF amplifier. The RF signals may be amplified by the RF amplifier and conveyed to the RF transmitter to generate a RF magnetic field. The positioning device may be configured to adjust the position of the subject in the FOV (field of view) of the MRI scanner 110. The positioning device may include a table to be moved to a desired position for or during the scan.

The central controller 130 may control the MRI scanner 110, the MRI auxiliary devices 120, the input/output device 140, and/or the data processing system 150. The central controller 130 may receive information from or send information to the MRI scanner 110, the MRI auxiliary devices 120, the input/output device 140, and/or the data processing system 150. For example, the central controller 130 may receive commands from the input/output device 140 provided by a user; the central controller 130 may process data input by a user via the input/output unit 140 and transform the data into one or more commands; the central controller 130 may control the MRI scanner 110, the MRI auxiliary devices 120, and/or the data processing system 150 according to the received commands or transformed commands; the central controller 130 may receive MR signals or data related to a subject from the RF receiver of the MRI scanner 110; the central controller 130 may send MR signals or data to the data processing system 150; the central controller 130 may receive processed data or constructed image from the data processing system 150; the central controller 130 may send processed data or constructed image to the input/output device 140 for displaying. In some embodiments, the central controller 130 may include a computer, a program, an algorithm, a software, a storage device, and a plurality of interfaces of the MRI scanner 110, the MRI auxiliary devices 120, the input/output device 140, and/or the data processing system 150.

The input/output device 140 may receive input and/or output information. The input and/or output information may include programs, software, algorithms, data, text, number, images, voices, or the like, or any combination thereof. For example, a user may input some initial parameters or conditions to initiate a scan. As another example, some information may be imported from an external resource including, for example, a floppy disk, a hard disk, a wired terminal, a wireless terminal, or the like, or any combination thereof. The output information may be transmitted to a display, a printer, a storage device, a computing device, or the like, or a combination thereof.

The data processing system 150 may process data relating to a subject and construct an image. In some embodiments, the data processing system 150 may be a program, an algorithm, and/or a software implemented on the central controller 130. In some embodiments, the data processing system 150 may be an independent system, coordinated with the central controller 130, including a processor, a controller, a memory, a display, a program, an algorithm, and/or a software. The data to be processed may be generated from the MRI scanner 110, or acquired from other external sources. For example, the data may be raw data generated from the MRI scanner 110; the data may be pre-treated by the central controller 130; the data may be pre-stored in a storage device of or accessible from the central controller 130; the data may be imported from an external resource including, for example, a floppy disk, a hard disk, a wired terminal, a wireless terminal, or the like, or any combination thereof. In some embodiments, the data to be processed and/or the image already constructed may include noise, artifacts, etc. The data processing system 150 may reduce or eliminate the noise, artifacts, etc., in the data or image. An exemplary artifact is Gibbs artifact, which may be also known as Gibbs effect/phenomenon, ringing artifact/effect, Gibbs ringing, truncation artifact, and/or spectral leakage artifact. Gibbs artifact may be caused by under-sampling in high spatial frequencies during data generation (i.e., data may be under sampled). As illustrated in a schematic drawing 160 with Gibbs artifact, alternating bright or dark lines/bands may appear parallel to and adjacent to the boundary of an area with abrupt change of signal intensity, the bright band in the schematic drawing 160. The multiple lines/bands may be regularly spaced, and fade as the distance to the boundary increases. In some embodiments, the data processing system 150 may reduce or eliminate Gibbs artifact. As illustrated in the schematic drawing 170, lines/bands may become less visible and the Gibbs artifact may be reduced or eliminated via data processing.

It should be noted that the above description of the imaging system is merely provided for the purposes of illustration, and not intended to limit the scope of the present disclosure. Many alternatives, modifications, and variations may be apparent to those skilled in the art. For example, the MRI scanner 110 and the MRI auxiliary devices 120 may be combined with a computed tomography (CT) scanner, or a positron emission tomography (PET) scanner. As another example, the function of the system may be varied or changed according to specific implementation scenarios. Merely by way of example, the data processing system 150 may include a noise removing unit, or other units.

Figure 2:
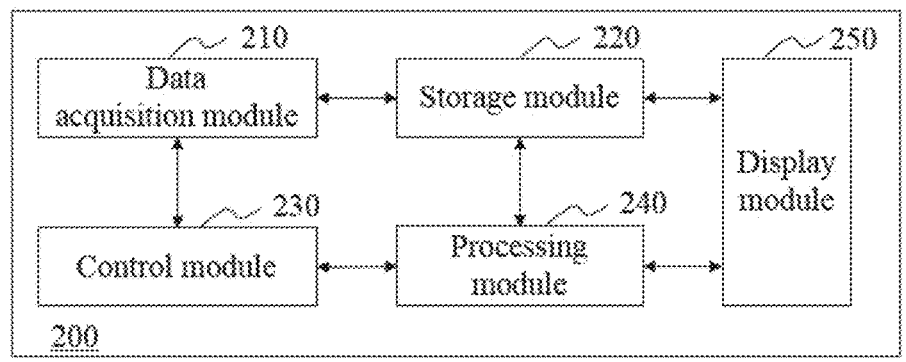
FIG. 2 is a block diagram depicting an image processing system according to some embodiments of the present disclosure.

FIG. 2 is a block diagram depicting an image processing system according to some embodiments of the present disclosure. The image processing system may acquire image data, process image data to reduce or remove artifact, and construct an image. The image processing system may include a data acquisition module 210, a storage module 220, a control module 230, a processing module 240, and an input/output module 250. The data acquisition module 210 may acquire image data. The image data acquired may be data in the Fourier region (or referred to as the spatial frequency space, or the k-space), data in the image domain (or space domain), or the like, or any combination thereof. The data may be acquired from a scan of a subject, or an external resource including, for example, a floppy disk, a hard disk, a wired terminal, a wireless terminal, or the like, or any combination thereof. In some embodiments, the data acquisition module 210 may include or communicate with an imaging device including, for example, an MRI device (for example, the MRI scanner 110 and the MRI auxiliary devices 120), a computed tomography (CT) device, a positron emission computed tomography (PET) device, etc. It should be noted that the imaging device may be a single-modality imaging device, or a multi-modality imaging device, or the like, or any combination thereof. Exemplary imaging devices may include a PET-MRI device, a CT-MRI device, a remote MRI device that may communicate with one or more of other modules via a wired or wireless connection, etc.

Data regarding a subject may be generated from the imaging device and acquired by the data acquisition module 210. In some embodiments, the data acquired may be undersampled. In some embodiments, the data acquisition module 210 may be connected with a terminal via a wired or wireless connection. Data may be transmitted from the terminal and received by the data acquisition module 210. In some embodiments, the data acquisition module 210 may include a data reading device to read data from a data storage medium including, for example, a floppy disk, a hard disk, an optical disk (e.g., a compact disc (CD), a digital versatile disc (DVD)), a flash memory, a universal serial bus (USB) flash disk, an secure digital (SD) card, a compact flash (CF) card, a memory stick, etc.

The storage module 220 may store data of the image processing system. The data stored may be a numerical value, a signal, an image, information of a subject, an instruction, an algorithm, or the like, or a combination thereof. The data stored may be in the Fourier region (or referred to as the spatial frequency space, or the k-space), or in the image domain. The data stored may be acquired by the data acquisition module 210, imported via the input/output module 250, generated in the processing module 240, or pre-stored in the storage module 220 during system initialization or before an operation of data processing. The storage module 220 may include a system storage (e.g., a disk) that is provided integrally (i.e. substantially non-removable), or a storage that is removably connectable to the system via, for example, a port (e.g., a UBS port, a firewire port, etc.), a drive (a disk drive, etc.), etc. The storage module 220 may include, for example, a hard disk, a floppy disk, selectron storage, random access memory (RAM), dynamic random access memory (DRAM), static random access memory (SRAM), bubble memory, thin film memory, magnetic plated wire memory, phase change memory, flash memory, a cloud disk, or the like, or a combination thereof. The storage module 220 may be connected or communicate with one or more of the data acquisition module 210, the control module 230, the processing module 240, and the display module 250. In some embodiments, the storage module 220 may be operationally connected with one or more virtual storage resources (e.g., cloud storage, a virtual private network, other virtual storage resources, etc.).

The control module 230 may be configured to control operation of the image processing system. In some embodiments, the control module 230 may control the operation of the data acquisition module 210 in data acquisition. For example, the control module 230 may control: the parameters setting (e.g., the magnetic field intensity, the magnetic field gradient, etc.) of an imaging device (if any), the production of the waveforms of the waveform generator in the imaging device (if any), and the position of a subject (if any) to be scanned, etc.

In some embodiments, the control module 230 may control the input or output of data into or from the storage module 220. In some embodiments, the control module 230 may control data transmitting among the data acquisition module 210, the storage module 220, the processing module 240, and/or the input/output module 250.

In some embodiments, the control module 230 may control the operation of the processing module 240 in data processing. For example, the control module 230 may control: the order of data calculation or processing, the adjustment of some parameters that may be used in the processing, the time or condition for triggering a data processing or ending a data processing, etc.

In some embodiments, the control module 230 may control the operation of the input/output module 250 for data display. For example, the control module 230 may control: the data display quality, image contrast, image resolution, image color, etc.

The control module 230 may perform system control according to some parameters, commands or instructions from other modules of the system. In some embodiments, the parameters, commands or instructions may be acquired from the storage module 220. In some embodiments, the control module 230 may receive commands from the input/output module 250 provided by a user, process information provided by a user via the input/output module 250, transform the information into specific commands, or the like, or a combination thereof. The control module 230 may be constructed based on an application-specific integrated circuit (ASIC), a microcontroller, a field programmable gate array (FPGA), an ARM, or the like, or any combination thereof.

The processing module 240 may process data and construct an image. The data may be acquired from the data acquisition module 210, or the storage module 220. The data to be processed may be in the Fourier region or in the image domain, or any combination thereof. Data in the image domain may be transformed to the Fourier region by way of Fourier transform; data in the Fourier region may be transformed to the image domain by way of inverse Fourier transform. In some embodiments, data transformation from the Fourier region to the image domain may be called as image reconstruction. In some embodiments, data processing may be performed in the Fourier region. Exemplary data processing in the Fourier region may include data filtering based on frequency, noise reduction, padding, interpolation, etc. In some embodiments, data processing may be performed in the image domain. Exemplary data processing in the image domain may include interpolation, logarithmic transforms, power law transforms, histogram equalization, etc. In some embodiments, data processing may be performed in both the Fourier region and image domain. For example, some data processing may be performed in the Fourier region and some data processing in the image domain. As another example, data processing in the Fourier region and the image domain may be performed alternately. In some embodiments, the processing module 240 may reduce or remove artifacts including Gibbs artifact, motion artifact, flow artifact, metal artifact, chemical shift artifact, partial volume artifact, wrap around artifact, or the like, or any combination thereof. For example, the processing module 240 may apply a plurality of algorithms (e.g., low-pass filtering in the Fourier region, interpolation in the Fourier region or image domain, total variation constrained data extrapolation, or the like, or any combination thereof) to reduce or remove Gibbs artifact.

The input/output module 250 may receive or output information. Merely by way of example, the input/output module 250 may provide data for display. The data displayed may include a value, a text, an image, and information of a subject. In some embodiments, the input/output module 250 may include a display for displaying data transmitted from the data acquisition module 210, the storage module 220, and/or the processing module 240. In some embodiments, the input/output module 250 may include an input device (e.g., a keyboard, a mouse, a touchscreen) to receive information from a user, transform the information to other types (e.g., transform a text to a string, transform a text to a command, transform a value to a parameter type that may be recognized, etc.), or send the information to other modules of the system.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage module 220 may be integrated into the processing module 240, or the input/output module 250 is unnecessary for the system.

Figure 3:
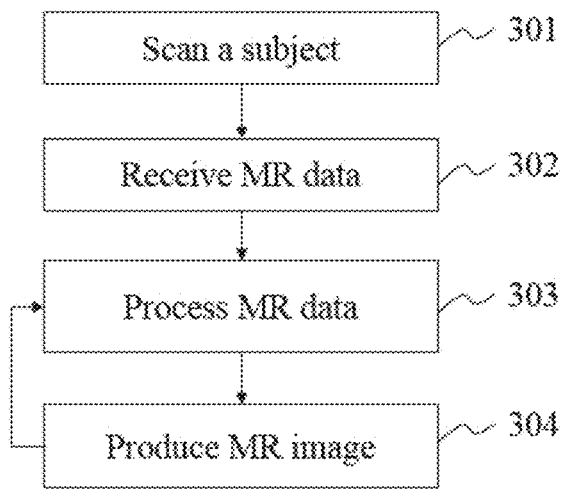
FIG. 3 is a flowchart illustrating a process of an MR scan according to some embodiments of the present disclosure.

FIG. 3 is a flowchart illustrating a process for an MR scan according to some embodiments of the present disclosure. The process may include scanning a subject 301; receiving MR data 302; processing MR data 303, and producing an MR image 304.

In step 301, an examination may be performed on a subject. The subject may be a human being, an animal, or a portion thereof including, for example, an organ, a texture, a region, an object, a lesion, a tumor, or the like, or any combination thereof. Merely by way for example, the object may include a head, a breast, a lung, a trachea, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof. In some embodiments, the examination may be an MR scan. In some embodiments, a number of settings may be used for scanning different types of objects, wherein each setting may include a plurality of parameters. Merely by way of example, the parameters may include the strength of main magnetic field, the strength of ladder magnetic field, the frequency of RF transmit signal, the scan mode, the gantry speed, or the like, or any combination thereof.

From the scan, the raw data corresponding to the subject may be acquired in step 302. In some embodiments, the raw data may be stored in the storage module 220 as numerical values. In some embodiments, the raw data may be exported and visualized in input/output modules 250 as matrices of numerical values. In some embodiments, the raw data may be expressed as data values in the k-space (or referred to as the frequency domain).

In step 303, the raw data obtained from step 302 may be processed by a plurality of procedures. In some embodiments, a rectifying procedure may be performed to correct or remove any unreliable and incorrect data values. In some embodiments, a noise filtering procedure may be performed to remove the noise produced during the scan. In some embodiments, the rectifying procedure and noise filtering procedure may either be performed before or after receiving the raw data. In some embodiments, the MR data may be analyzed and processed in the k-space. In some embodiments, a filter may be implemented to remove data values in unwanted frequency ranges. Merely by way of example, a low pass filter may be used to remove data values in high-frequency ranges. As used herein, the low pass filter may refer to a filter passing low-frequency signals while attenuating (reducing the amplitude of) signals with frequencies higher than a cut-off frequency. In some embodiment, the raw data may be padded (for example, zero-padded) to reduce mosaic effect according to some embodiments of present disclosure. In some embodiments, the data values may be classified into several regions based on their frequencies and different procedures may be performed on different ranges of frequencies.

In some embodiments, an objective function (also referred to as cost function) may be constructed based on the size of the raw data matrix, the order of the objective function, a kernel function of the objective function, the numerical range of the raw data, the significance of Gibbs artifact and/or mosaic effect, or the like, or any combination thereof. In some embodiment, in order to obtain a satisfactory solution of the objective function, at least some raw data values may be modified. The modification may be subject to a constraint. Merely by way of example, the raw data may be classified into several regions based on their frequencies, and an objective function may be constructed so that data in only some regions may be modified.

After the raw data is processed, the processed data may be reconstructed to generate an image in step 304. Merely by way of example, the reconstruction algorithm of the image may include a Fourier Transform (FT), a Fast Fourier Transform (FFT), an Inverse Fourier Transform (IFT), an Inverse Fast Fourier Transform (IFFT), a 2d Fourier Transform, a Discrete Fourier Transform (DFT), an iterative reconstruction, a backward projection, or the like, or any combination thereof.

As shown in FIG. 3, in some embodiments, an image may be updated based on previous images and other factors. In some embodiments, a process may be implemented to transform the image back to data values in the k-space and the data values in the preceding iteration (also referred to as old values) may be modified based on the data values obtained in said process (also referred to as new values). In some embodiments, the loop may include some parameters to assess the effect of the new values on the old values. For instance, a contribution factor may indicate the contribution or effect of the new values on the old values. In some embodiments, the contribution factor may depend on the frequency of data values. After the data values are modified, the new image may then be generated based on the updated data values. In some embodiments, an image in a next iteration may be based on an image in a current iteration, i.e. an image may be iteratively dependent on the image obtained in a previous iteration. In some embodiments, an image may be iteratively dependent on images in a plurality of previous iterations.

In some embodiments, the feedback loop may be achieved only by software. In some embodiments, the loop may be achieved by both electronic circuits and software.

This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments. It should be appreciated for those skilled in the art that the disclosed method may be used in a plurality of examinations including a digital subtraction angiography (DSA) system, a magnetic resonance imaging (MRI) system, a magnetic resonance angiography (MRA) system, a computed tomography (CT) system, a computed tomography angiography (CTA) system, an ultrasound scanning (US) system, a positron emission tomography (PET) system, a single-photon emission computerized tomography (SPECT) system, a CT-MR system, a CT-PET system, a CE-SPECT system, a DSA-MR system, a PET-MR system, a PET-US system, a SPECT-US system, a TMS (transcranial magnetic stimulation)-MR system, an US-CT system, an US-MR system, an X-ray-CT system, an X-ray-MR system, an X-ray-portal system, an X-ray-US system, a Video-CT system, a Vide-US system, or the like, or any combination thereof.

Figure 4:
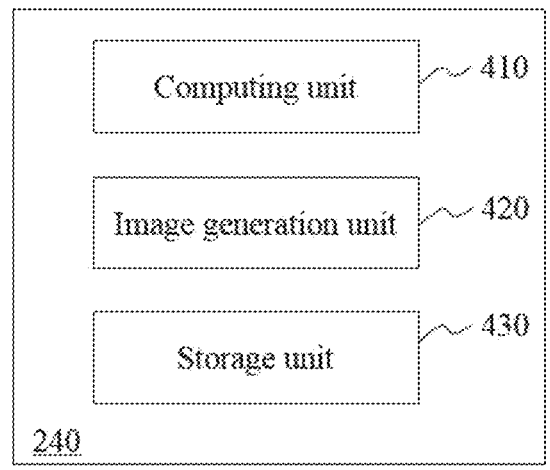
FIG. 4 illustrates a block diagram of the processing module according to some embodiments of the present disclosure.

FIG. 4 illustrates a block diagram of the processing module according to some embodiments of the present disclosure. As shown in the figure, the processing module 240 may include a computing unit 410, an image generation unit 420, and a storage unit 430. The computing unit 410 may calculate different kinds of information received from, for example, the control module 230, the storage module 220, and/or the input/output module 250. The information from the control module 230 may include information about the MRI system 110, the strength of gradient field, the RF sections, the subject position 120, or the like, or any combination thereof. In some embodiments, the computing unit 410 may calculate the data values in the k-space. In some embodiments, the data values in the k-space may be acquired from a plurality of channels. The plurality of channels may be associated with a single RF receiver of a MRI system. In some embodiments, the plurality of channels may be associated with more than one RF receiver of an MRI system. The computing unit 410 may combine the data values in different channels. In some embodiments, the data values in the k-space may be acquired from a single channel. In some embodiments, the computing unit 410 may calculate coefficients of a filter generated based on at least one window function. In some embodiments, the computing unit 410 may calculate coefficients and/or formula of an objective function. In some embodiments, the computing unit 410 may calculate the values and convergence rate of the objective function.

The image generation unit 420 may process the data such as magnetic resonance (MR) signals acquired from a subject and reconstruct them into one or more MR image. The image generation unit 420 may employ different kinds of imaging reconstruction techniques for the image reconstruction procedure. The image reconstruction techniques may include a Fourier Transform, a Fast Fourier Transform, an Inverse Fourier Transform, a 2d Fourier Transform, a Discrete Fourier Transform (DFT), an iterative reconstruction, a backward projection, or the like, or any combination thereof.

In some embodiments, the image generation unit 420 may include an iterative reconstruction to update the image until a condition is satisfied. In some embodiments, the condition may relate to an objective function.

The storage unit 430 may store the information that may be used by the computing unit 410 and/or the image generation unit 420. The information may include programs, software, algorithms, data, text, number, images, etc. These examples are provided here for illustration purposes, and not intended to limit the scope of the present disclosure. The storage unit 430 may store algorithms including, for example recursion, a nonlinear conjugate gradient method, a bisection method, an exhaustive search (or brute-force search), a greedy algorithm, a divide and conquer algorithm, a dynamic programming method, an iterative method, a branch-and-bound algorithm, a backtracking algorithm, or the like, or any combination thereof.

It should be noted that the above description of the processing module is merely provided for the purposes of illustration, and not intended to limit the scope of the present disclosure. For persons having ordinary skills in the art, multiple variations or modifications may be made under the teachings of the present disclosure. For example, the assembly and/or function of module unit may be varied or changed. In some embodiments, the computing unit 410 and the image generation unit 420 may share one storage unit 430. In some embodiments, the computing unit 410 and the image generation unit 420 may each have their own storage units, respectively. However, those variations and modifications do not depart from the scope of the present disclosure.

Figure 5:
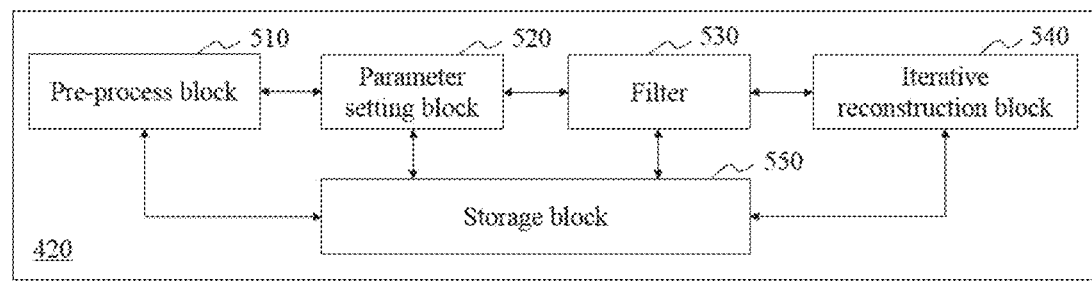
FIG. 5 illustrates a block diagram of the image generation unit according to some embodiments of the present disclosure.

FIG. 5 illustrates a block diagram of the image generation unit according to some embodiments of the present disclosure. As shown in the figure, the image generation unit may include a pre-process block 510, a parameter setting block 520, a filter 530, an iterative reconstruction block 540, and a storage block 550. The pre-process block 510 may perform some pre-processing to the raw data. The pre-processing may include image normalization, image segmentation, image reconstruction, image smoothing, suppressing, weakening and/or removing a detail, a mutation, a noise, or the like, or any combination thereof.

The data treated by the pre-process block 510 may be sent to the parameter setting block 520. The data may contain the image-related data in the k-space, as well as various types of data related to the subject. The image-related data in the k-space may be undersampled. For example, the image-related data in the k-space may occupy a part of the k-space. The parameter setting block 520 may set the values of various parameters used in the process of image generation. The parameters may relate to the subject, including but not limited to, the age, weight, height, heart rate, blood oxygen level, blood pressure. The parameters to be set by the parameter setting block 520 may relate to the part or region in the k-space. For example, the image-related data in the k-space may occupy a part D1 of the k-space. The part D1 may have a dimension of M1×N1. In some embodiments, M1 may be equal to or different from N1. The parameter setting block 520 may designate another region D2, of dimension M2×N2, inside the part D1. In some embodiments, M2 may be equal to or different from N2. In some embodiments, M1 may be equal to or larger than M2. In some embodiments, N1 may be equal to or larger than N2. The parameters setting block 520 may also designate a part D3, of dimension M3×N3, containing the region D1. In some embodiments, M3 may be equal to or different from N3. In some embodiments, M1 may be equal to or smaller than M3. In some embodiments, N1 may be equal to or smaller than N3. In some embodiments, the parameter setting block 520 may set the values of some parameters related to the filter 530 such as, for example, the width of the pass band (PB), the width of the transition band (TB), and the threshold value for the filter 530.

The filter 530 may treat the image-related data in the k-space. In some embodiments, the filter 530 may be a low-pass filter. In some embodiments, the filter 530 may be a band pass filter (BPF). The filter 530 may be characterized by its pass band (PB), transient band (TB), and the transient function within the transient band.

Figure 8:
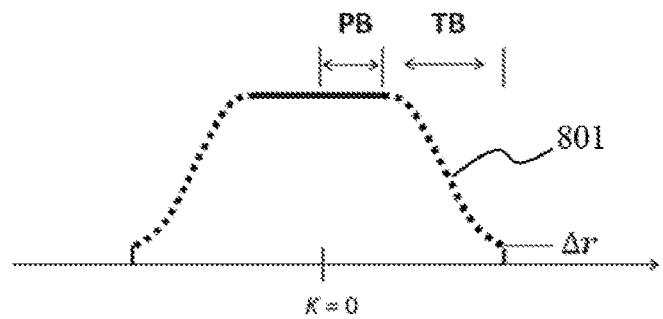
FIG. 8 is an exemplary one-dimensional prototype low-pass filter according to some embodiments of the present disclosure.
Figure 9:
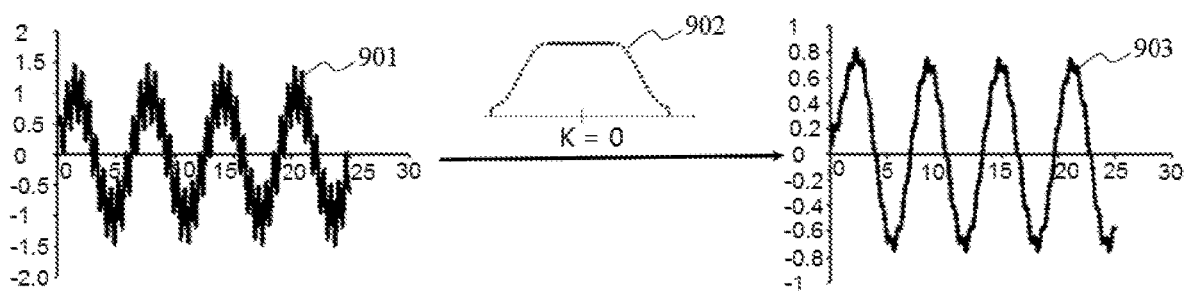
FIG. 9 illustrates an exemplary one-dimensional prototype low-pass filter according to some embodiments of the present disclosure.

An exemplary one-dimensional prototype low-pass filter may be demonstrated as in FIG. 8, and the effect of an exemplary one-dimensional prototype low-pass filter may be demonstrated as in FIG. 9. Here after normalization the strength of the filter inside the pass band is one, and the pass band together with the transient band may satisfy the following relation specified in Equation (1):

$$2(PB+TB)=1.0. \qquad (1)$$

In some embodiments, a weak filtering effect may be employed. For example, TB may be no less than 0.1. In some embodiments, TB may be no less than 0.15. In some embodiments, TB may be no less than 0.2. The transient function f(k) may be a combination of trigonometric functions, inverse trigonometric functions, exponential functions, logarithmic functions, polynomial functions, or the like, or a combination thereof. For example, the transient function may be given in the form of a Hanning window. As another example, the transient function may be given in the form of a Turkey window.

The threshold value after normalization Δr may indicate the effect of diminishing high-frequency components of the data. The threshold for high frequency component may be related to the pass band (PB) and/or the transition band (TB). For example, the threshold for high frequency component may be set as the sum of pass band and transition band. In some embodiments, a weak filtering effect may be employed. For example, Δr may be equal to or larger than 0.3. In some embodiments, Δr may be equal to or larger than 0.2. In some other embodiments, Δr may be equal to or larger than 0.1.

The filter 530 may be generated by expanding multiple one-dimensional prototype low-pass filters. In some embodiments, these multiple one-dimensional prototype low-pass filters may be mutually orthogonal to each other. In other words, a first one-dimensional prototype low-pass filter may be along a first direction in the k-space, a second one-dimensional prototype low-pass filter may be along a second direction orthogonal to the first direction. For example, a first one-dimensional prototype low-pass filter may be along the k_x direction in the k-space, whereas a second one-dimensional prototype low-pass filter may be along the k_y direction that is orthogonal to the k_x direction.

The filter 530 may also be generated by expanding the one-dimensional prototype low-pass filter in a rotation-invariant way. For example, all the points in the k-space with the same radial coordinate squared $k_x^2+k_y^2$ may have the same filtering effect.

The filtered image-related data in the k-space by the filter 530 may be sent to the iterative reconstruction block 540. The iterative reconstruction block 540 may be configured to generate an expanded image-related data in the k-space. The iterative reconstruction block 540 may be based on an objective function on the image data in the k-space. The reconstruction block 540 may utilize an algorithm in connection with the objective function. In some embodiments, the algorithm may operate to reduce or minimize the objective function. The algorithm may be of an iterative type. In some embodiments, the algorithm may be a non-linear conjugate gradient algorithm, a Powell method, a downhill simplex method, a gradient descent method, a descent simplex method, a deepest gradient descending method, a conjugate gradient method, a pseudo-Newton method, a quasi-Newton method, a least-squares and Gauss-Newton method, a Broyden-Fletcher-Goldfarb-Shannon (BFGS) method, a limited-memory Broyden-Fletcher-Goldfarb-Shannon (L-BFGS) method, a simulated annealing method, an ant colony optimization (ACO) method, a genetics method, a Levenberg-Marquardt optimization method, a geometric hashing method, a particle swarm optimization (PSO) method, a firefly algorithm (FA) method, or the like, or a combination thereof. The algorithm may also be of stochastic type. In some embodiments, the algorithm may be a Monte-Carlo (MC) method, a fast Monte-Carlo method, an analog Monte-Carlo method, a Non-analogue Monte-Carlo method, a resampling method, or the like, or a combination thereof. The objective function may relate to the total variation (TV) of the image data in the k-space. A total variation of a first order may be the sum of the modulus of jumps between neighboring pixels of a reconstructed image I(x, y). A total variation of a first order may be referred as:

$$TV_1(I)=\Sigma_{y=0}^{N}\Sigma_{x=0}^{N}|I(x,y)-I(x-1,y)|+|I(x,y)-I(x,y-1)|. \qquad (2)$$

Calculation of the TV value according to Equation (2) uses the first-order derivative of the image with respect to the x-direction and the y-direction. In some embodiments, the total variation may be based on second-order derivatives. A total variation of a second order may be referred as:

$$TV_1(I)=\Sigma_{y=0}^{N}\Sigma_{x=0}^{N}\sigma*(|I(x,y)-I(x-1,y)|+|I(x,y)-I(x,y-1)|)+(1-\sigma)*(|I(x-1,y)-2*I(x,y)+I(x+1,y)|+|I(x,y-1)-2*I(x,y)+I(x,y+1)|+|I(x,y)-I(x-1,y)-I(x,y-1)+I(x-1,y-1)|), \qquad (3)$$

where σ∈[0 1] may be a weighting factor. The weighting factor may be used to tune the smoothness of an image. For instance, if a decreases from one to zero, the image may allow for the intensity gradients in an image and yield more naturally looking solutions.

The objective function may relate to the energy of the image data in k-space. The energy of the image data in the k-space may be given as the L-p norm of the image data in a region of the k-space, where p≥1. The reduction or minimization of the objective function may be subject to a constraint. For example, the constraint may be such that the image data inside the part D2 remain unchanged during the iteration process. As another example, the constraint may be such that the image data inside the part D3 have a fixed energy.

The storage block 550 may be configured to connect to the pre-process block 510, the parameter setting block 520, the filter 530, and the iterative reconstruction block 540. The storage block 550 may store various types of data, such as the image, the parameters used in the parameter setting block 520, image-related data in the k-space, or the like, or a combination thereof. The storage block 550 may store data by the way of electric, magnetic, optical energy, or virtual storage resources, etc. The storage block 550 that store data by the way of electric energy may include Random Access Memory (RAM), Read Only Memory (ROM), flash memory, or the like, or any combination thereof. The block 550 that stores data by the way of magnetic energy may include a hard disk, a floppy disk, a magnetic tape, a magnetic core memory, a bubble memory, a USB flash drive, or the like, or any combination thereof. The storage block 550 that store data by the way of optical energy may include Compact Disk (CD), Video Compact Disk (VCD), or the like, or any combination thereof. The storage block 550 that stores data by the way of virtual storage resources may include cloud storage, a virtual private network, and/or other virtual storage resources. The method to store data may include sequential storage, link storage, hash storage, index storage, or the like, or any combination thereof.

It should be noted that the above descriptions about the image generation unit is merely an example, should not be understood as the only embodiment. Obviously, to those skilled in the art, after understanding the basic principles of the connection between different blocks, and connection between the blocks may be modified or varied without departing from the principles. The modifications and variations are still within the scope of the current disclosure described above. In some embodiments, these blocks may be independent, and in some embodiments, part of the blocks may be integrated into one block to work together.

Figure 6:
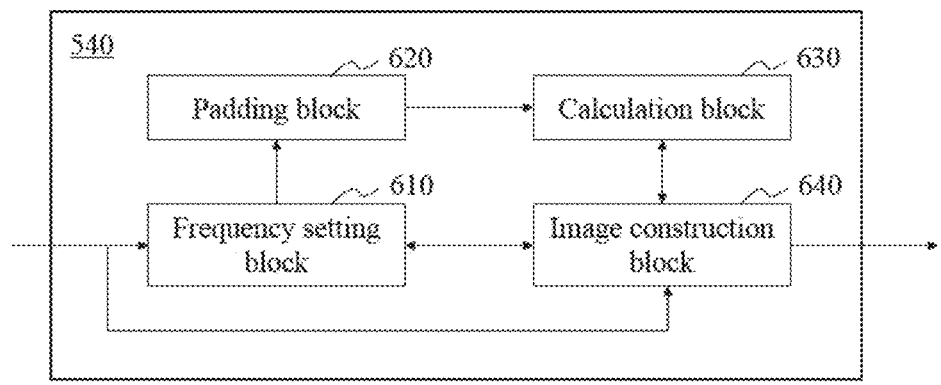
FIG. 6 illustrates a block diagram of an iterative reconstruction block according to some embodiments of the present disclosure.

FIG. 6 illustrates a block diagram of an iterative reconstruction block 540 according to some embodiments of the present disclosure. As shown in the figure, the iterative reconstruction block 540 may include a frequency setting block 610, a padding block 620, a calculation block 630, and an image construction block 640. For the filtered image-related data in the k-space, an area in the k-space, called the natural region of the data, may be specified. The natural region of the data may be the set of coordinates in the k-space where the data has been given. In some embodiments, the natural region of the data in the k-space may be a part of dimension M1×N1 (see part 1002 as in FIG. 10A for an illustration). The frequency setting block 610 may be used to specify an inner region inside the part for the data. The inner region may be a region of dimension M2×N2, where M2≤M1, N2≤N1. In some embodiments, the inner region may be a combination (e.g., disjoint union) of several smaller regions inside the natural region.

The padding block 620 may fill data into an area outside the natural region of the data in k-space. In some embodiments, zero padding may be implemented on an area outside the natural region. In some embodiments, a non-zero padding may be implemented on an area outside the natural region. For example, the padding block 620 may assign a nonzero constant to an area outside the natural region. The data given on the extended region may be sent to the calculation block 630 for further processing.

The calculation block 630 may perform various types of calculation on the data in image domain or an image-related data in the k-space. In some embodiments, the first order total variation of data in the image domain may be calculated by the calculation block 630. For example, for an image data I(x, y), the first order total variation of the image I(x, y) may be defined in Equation (2).

In some embodiments, the second order total-variation of an image may be calculated by the calculation block 630. For example, for an image I(x, y), the second order total variation of the image I(x, y) may be defined in Equation (3).

The calculation block 630 may also perform Fourier transform on an image I, denoted as F(I). In some embodiments, the Fourier transform may be implemented as a Fourier transform matrix M_F transforming an image data from the image space to the corresponding image-related data in the k-space.

The image construction block 640 may utilize the output of padding block 620 and the calculated quantities from calculation block 630 for use in a searching algorithm. The searching algorithm may be implemented by the image construction block 640 to reduce or minimize an objective function on the image data in the image domain. In some embodiments, the algorithm may be of an iterative type. In some embodiments, the algorithm may be a non-linear conjugate gradient algorithm, a Powell method, a downhill simplex method, a gradient descent method, a descent simplex method, a deepest gradient descending method, a conjugate gradient method, a pseudo-Newton method, a quasi-Newton method, a least-squares and Gauss-Newton method, a Broyden-Fletcher-Goldfarb-Shannon (BFGS) method, a limited-memory Broyden-Fletcher-Goldfarb-Shannon (L-BFGS) method, a simulated annealing method, an ant colony optimization (ACO) method, a genetics method, a Levenberg-Marquardt optimization method, a geometric hashing method, a particle swarm optimization (PSO) method, a firefly algorithm (FA) method, or the like, or a combination thereof. The algorithm may be of a stochastic type. In some embodiments, the algorithm may be a Monte-Carlo (MC) method, a fast Monte-Carlo method, an analog Monte-Carlo method, a Non-analogue Monte-Carlo method, a resampling method, or the like, or a combination thereof.

The objective function may relate to the total variation and/or the energy of the image data in the k-space. The minimization of the objective function may be subject to a constraint. The constraint may be imposed upon the targeted image data, so that the targeted image data has a specific behavior in certain region of k-space. For example, the constraint may be such that the image data inside the region D1 remain unchanged during the iteration process. As another example, the constraint may be such that the image data inside the region D3 have a fixed energy.

In some embodiments, the following objective function $G(\rho)$ on the image data p in the image space may be implemented:

$$G(\rho)=\|P_1(F\rho-Y)\|_2^2+\lambda_1 TV_1(\rho)+\lambda_2 TV_2(\rho), \qquad (4)$$

where $\lambda_1$ and $\lambda_2$ may be real constants. In some embodiments, the values of $\lambda_1$ and/or $\lambda_2$ may be between zero and one. Merely by way of example, the values of $\lambda_1$ and $\lambda_2$ may be chosen so that $\lambda_1=3\lambda_2$. F denotes the Fourier Transform operator, Y denotes the image-related data in the natural region of the k-space.

$P_1$ may stand for a matrix used to choose data points in the k-space. In some embodiments, the data points chosen by $P_1$ may be allowed to change during the iterative searching for a solution of the objective function. Merely by way of example, the solution may be such that the value of the objective function may be minimal. As another example, the solution may be such that the change in the value of the objective function in the two or more consecutive iterations may be equal to or smaller than a threshold. As a further example, the solution may be obtained after a certain number of iterations. The iterations may terminate when the solution is obtained.

In some embodiments, the following constraint on the image data p in image space may be implemented $$P_2(F\rho-Y)=0, \qquad (5)$$

where $P_2$ may be a matrix used to choose a set of data points in the k-space. For example, the image-related data in the k-space may be within a part D1 of the k-space. The part D1 may have a dimension of M1×N1. The parameter setting block 520 may designate region D2, of dimension M2×N2, within the part D1. The parameters setting block 520 may also designate a part D3, of dimension M3×N3, containing the part D1. In some embodiments, $P_2$ may be used to specify that the data points inside D2 remain unchanged during the iterative steps of the searching algorithm.

A searching algorithm to minimize the objective function may be implemented in the image construction block 640 to generate an image in the image space. The image may be output to the patient, or to the doctor, or to anyone related to the image. The image may be sent to a server, a cloud server, a network, a database for storage. The image may be subject to further process such as normalization or denoising.

It should be noted that the above descriptions about the iterative reconstruction block is merely an example, should not be understood as the only embodiment. Obviously, to those skilled in the art, after understanding the basic principles of the connection between different blocks, and connection between the blocks may be modified or varied without departing from the principles. The modifications and variations are still within the scope of the current disclosure described above. In some embodiments, these blocks may be independent, and in some embodiments, part of the blocks may be integrated into one block to work together.

Figure 7:
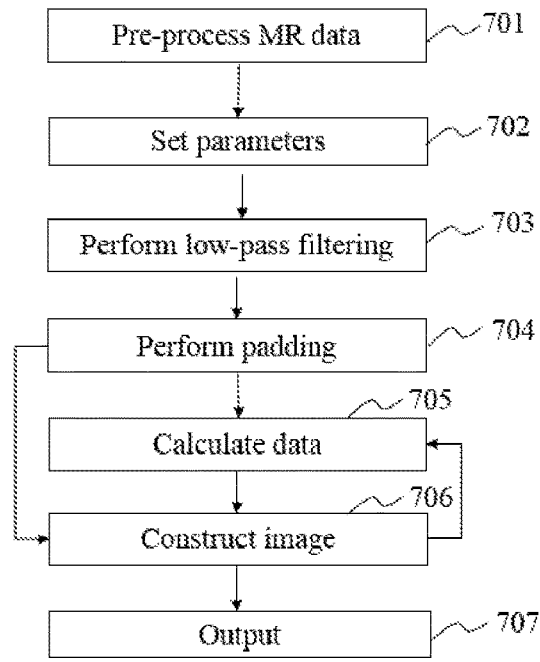
FIG. 7 is an exemplary flowchart illustrating a process for removing the Gibbs artifact from an image according to some embodiments of the present disclosure.

FIG. 7 is an exemplary flowchart illustrating a process for reducing or removing the Gibbs artifact from an image according to some embodiments of the present disclosure.

In step 701, image data or an image-related data in the k-space may be pre-processed. The pre-processing may include image normalization, image segmentation, image reconstruction, image smoothing, suppressing, weakening and/or removing a detail, a mutation, a noise, or the like, or any combination thereof.

In step 702, various parameters related to the image-related data in k-space may be set. The parameters may be related to the subject, including but not limited to, the age, weight, height, heart rate, blood oxygen level, blood pressure. The parameters to be set may also be related to the specification of the region in the k-space. For example, the natural region of the image-related data in the k-space may be a part D1 of dimension M1×N1. In some embodiments, parameters for an inner region D2 inside the part may be specified. For example, the inner region D2 may be a region of dimension M2×N2, where M2≤M1, N2≤N1. In some embodiments, the inner region may be a disjoint union of several smaller regions inside the natural region. In some embodiments, parameters for an outer region D3, of dimension M3×N3, containing the natural region D1, may be designated as well.

An exemplary illustration of setting a larger region containing the natural region may be seen in FIG. 10A where the image-related data in the k-space occupy. The region 1002 is the natural region where the image-related data in k-space may originally be specified. The region 1001 may be the extended area outside the region 1002 in k-space for providing further process of the image related data. For example, zero padding may be performed on the region 1001.

FIG. 10B shows an exemplary illustration of setting a larger region containing the natural region and setting a smaller region inside the natural region where the image-related data in the k-space occupy. The region 1002 may be the natural region where the image-related data in k-space may originally be specified. The region 1001 may be the extended area outside the region 1002 in the k-space for providing further process of the image related data. For example, padding may be performed on the region 1001. The region 1003 may be inner region inside the natural region 1002. The inner region 1003 may be subject to a constraint during the iteration steps of the searching algorithm, which may be described below.

In step 703, a filtering may be applied on the image-related data in k-space. In some embodiments, the filtering may be a low-pass filtering. Some parameters of the low-pass filtering may be specified in step 702. For example, the width of the pass band (PB), the width of the transition band (TB), and the threshold value for the low-pass filtering may be specified in step 702. In some embodiments, these parameters may be specified in step 703.

In step 704, a procedure of padding may be performed on the filtered image-related data in k-space. In some embodiments, the filtered image-related data lies in a natural region. A zero-padding may be performed on the filtered image-related data by setting zero value in a neighboring area of the natural region. For example, the filtered image-related data may lie in a natural region as 1002 of FIG. 10A. A zero-padding may be performed on the region 1001. Alternatively, a nonzero-padding may be performed on the region 1001, i.e. a nonzero constant may be set on the region 1001. The padded image-related data in the k-space may be sent to step 705 for further processing, or it may be sent to step 706 for image construction.

In step 705, a process for performing substantially the minimization of an objective function for the image-related data in the k-space may be implemented. Here the process of minimization may be realized if the difference between the achieved objective function values and theoretical minimal objective function values is below a threshold. The objective function may relate to the total variation of the image data in the k-space. The total variation may be a first order total variation, a second order total variation or the like, or any combination thereof. The first order total variation and the second order total variation may be shown in Equation (2) and Equation (3), respectively. The objective function may relate to the energy of the image data in the k-space. The energy of the image data in the k-space may be given as an L-p norm of the image data in the k-space, where p≥1. The minimization of the objective function may be subject to a constraint. For example, the constraint may be such that the image data inside the region D1 remain unchanged during the iteration process. As another example, the constraint may be such that the image data inside the region D3 have a fixed energy.

In step 706, an image based on the resulted data in k-space may be generated. The way of generating an image from the data in the k-space may be familiar to those skilled in the art. If the image based on the resulted data in k-space is not satisfactory, the data in k-space may be sent back to step 705 for further process. If the image based on the resulted data in k-space is satisfactory, then the image will be sent to step 707 for outputting.

It should be noted that the flowchart of a process for removing the Gibbs artifact from an image described above is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure. For example, in step 701, the image related data in the k-space may be a combination of data from a plurality of channels, which may be referred to as channel fusion. As another example, in step 701, the image related data in the k-space may be from a single channel. In some embodiments, the process of channel fusion to obtain the image related data in the k-space via a plurality of channels may lose the phase information of the image, such as by using the method of Sum of Square (SoS). Then the step 704 of zero-padding may be performed before the process of channel fusion. Steps 701 through 707 may be performed sequentially at an order other than that described above in FIG. 7. At least two steps of steps 701 through step 707 may be performed concurrently. Steps 701 through 707 may be merged into a single step or divided into a number of steps. In addition, one or more other operations may be performed before/after or in performing steps 701 through 707. In some embodiments, at least one of steps 701 through 707 may be unnecessary and may be omitted.

FIG. 11A illustrates an exemplary flowchart of a process for an image reconstruction according to some embodiments of the present disclosure. Data may be acquired in step 1101 directly through a data scan process in step 201, or it may be obtained through a plurality of processes after the data scan process in step 201. The processes may include but not limit to low-pass filtering, padding, a frequency analysis, or the like, or a combination thereof. The data may be obtained from a storage medium of or accessible by the data processing system 150.

In some embodiments, the image reconstruction described in the present disclosure may be implemented by one or more modules, units or blocks in the system of the present disclosure. In some embodiments, the image reconstruction may include a step of updating the image by changing the position of the scanned subject.

Based on the data acquired in step 1101, the parameters may be set in step 1104. In some embodiments, the parameters may relate to the performance of the image reconstruction. In some embodiments, the parameters may include one or more parameters or properties of an objective function. Merely by way of example, one or more parameters or properties of the objective function may include order, condition of convergence, kernel function, numerical range of the objective function, or the like, or any combination thereof.

During the first iteration, an initial image may be acquired in step 1110 by the input relating to the initially estimated image in step 1107, while in any other iteration, the image in step 1110 may be updated by a reconstructed image generated from the previous iteration.

After the image in step 1110 is updated, the value of the objective function may be calculated in step 1113. The calculation may include substituting the magnitude of at least a portion of the updated image into the objective function. In some embodiments, the magnitude of the updated image may be determined by the grey level or intensity of a plurality of pixels inside the updated image. As shown in FIG. 11A, a determination may be made in step 1116 to determine whether a condition is satisfied. Merely by way of example, the condition may be such that the value of the objective function may be minimal. As another example, the condition may be such that the change in the value of the objective function in the two or more consecutive iterations may be equal to or smaller than a threshold. As a further example, the condition may be satisfied after a certain number of iterations. If the condition is satisfied, the iteration may terminate and the current image may be stored as a target image in step 1119 so that the image may be output as a final image. If the condition is not satisfied, the process may proceed back to step 1110. In some embodiments, the image obtained in an iteration may be updated based on either the image or the value of the objective function in the preceding iteration. After the image is updated in step 1110 in the new iteration, the similar process may be performed until the condition is satisfied in step 1116. The image satisfying the condition may then be output as the final image.

In some embodiment, the objective function may take the following form:

$$G(\rho)=\|P_1(F\rho-Y)\|_2^2+\lambda_1 TV_1(\rho)+\lambda_2 TV_2(\rho), \quad (6)$$

subject to $$P_2(F\rho-Y)=0. \quad (7)$$

In some embodiment, the objective function may take the following form:

$$G(\rho)=\|P_1(F\rho-Y)\|_2^2+\lambda_1 TV_1(\rho)+\lambda_2 TV_2(\rho)+\lambda_3\|P_2(F\rho-Y)\|_2^2, \quad (8)$$

where F may denote the Fourier Transform matrix, p may denote the estimated image, Y may denote the processed data values in the k-space obtained in step 1101, $P_1$ may stand for a matrix used to choose data points in the k-space. In some embodiments, the data points chosen by $P_1$ may be allowed to change during a search for a solution of the objective function. The search may proceed iteratively. $P_2$ may be a matrix used to choose a set of data points in the k-space. For example, the image-related data in the k-space may be within a region D1 of the k-space. The region D1 may have a dimension of M1×N1. The parameter setting block 520 may designate a region D2, of dimension M2×N2, within the region D1. In some embodiments, $P_2$ may be used to specify that the data points inside D2 remain unchanged during the searching process. $TV_n$ may denote an nth-order total variation reconstruction calculation. In some embodiments, $\lambda_1$, $\lambda_2$ and $\lambda_3$ may be real numbers. Merely by way of example $\lambda_1$ and $\lambda_2$ may be smaller or equal to 1, while $\lambda_3$ may be greater 5. The coefficient $\lambda_3$ may be referred to as the constraint strength.

Additionally, $\|x\|_2$, or denoted as L2-norm, may be defined as:

$$\|x\|_2=\sqrt{\Sigma_j|x_j^2|}. \quad (9)$$

As shown in the formulae (6) and (7), the converging of the objective function may include two steps: setting the estimated image ρ in D2 to be the Fourier Transform of the processed data values Y of the corresponding region and keeping it unchanged; and updating the estimated image ρ in D1 and calculating the value of the objective function in formula (6) until a condition is satisfied. In some embodiments, the condition may be satisfied when the value of the objective function is smaller than a threshold. In some embodiments, the condition may be satisfied when a minimum value of the objective function is obtained. In some embodiments, the condition is satisfied when the change in the value of the objective function in a number of iterations (e.g., a number of successive iterations) is below a threshold. In some embodiments, the condition is satisfied when the difference between the value of the objective function and a target value is below a threshold. In some embodiments, the condition is satisfied when a specified number of iterations are performed.

Refer to formula (8), the converging of the objective function may include a step of updating the estimated image ρ in both D1 and D2 and calculating the value of the objective function in formula (8) until a condition is reached. In some embodiments, the change of data values of estimated image ρ in D2 may be to a less extent than the change of the data values in D1 during the iteration process.

It should be noted that the flowchart of a process for removing the Gibbs artifact from an image described above is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure. For example, step 1101, step 1104, step 1107, step 1110, step 1113, step 1116 and step 1119 may be performed sequentially at an order other than that described above in FIG. 11A. At least two steps of step 1101, step 1104, step 1107, step 1110, step 1113, step 1116 and step 1119 may be performed concurrently. Step 1101, step 1104, step 1107, step 1110, step 1113, step 1116 and step 1119 may be merged into a single step or divided into a number of steps.

In addition, one or more other operations may be performed before/after or in performing step 1101, step 1104, step 1107, step 1110, step 1113, step 1116 and step 1119. At least one of step 1101, step 1104, step 1107, step 1110, step 1113, step 1116 and step 1119 may be unnecessary and may be omitted.

Figure 11B:
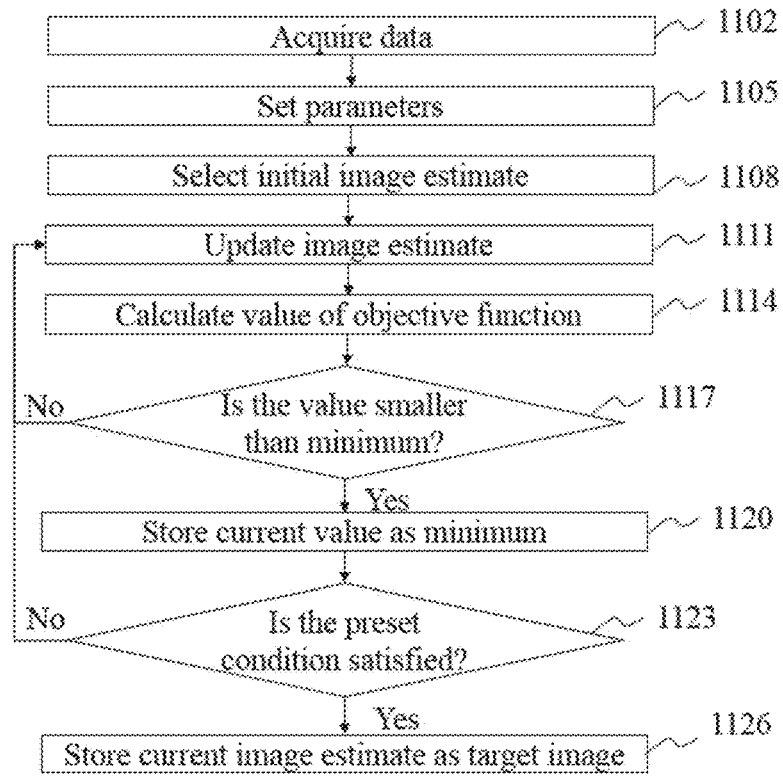

FIG. 11B illustrates another exemplary flowchart of a process for an image reconstruction according to some embodiments of the present disclosure. Step 1102, step 1105, step 1108, step 1111, and step 1114 may be the same as step 1101, step 1104, step 1107, step 1110, and step 1113 of FIG. 11A, respectively.

Before the first iteration, a current smallest value used in step 1117 and step 1120 may be set to zero or any appropriate values. The current smallest value may represent the smallest value of the objective function of all the values from first iteration to the current iteration. After the value of the objective function is calculated in step 1114, a determination may be made in step 1117 to determine whether the value of the objective function is smaller than the current smallest value. If the value of objective function is smaller than the current smallest value, the current smallest value may be replaced and updated by the value of the objective function in step 1120. If the value of objective function is not smaller than the current smallest value, the process may proceed back to step 1111.

After at least a value of the objective function is smaller than the current smallest value, a determination in step 1123 similar to that of FIG. 11A may be performed, and similar iterative process may follow as described elsewhere in present disclosure. Once the condition is satisfied, the current image may be saved as the target image in step 1126, the image may then be output as the final image.

In some embodiments, step 1105 may be performed after the image is updated in step 1111. In some embodiments, the parameters in step 1105 may be set and changed in every iteration. Merely by way of example, the order, condition of convergence, kernel function, and numerical range of the objective function, or the like, or any combination thereof may be changed in every iteration.

In some embodiments, the objective function in formula (6), formula (7), and formula (8) may be used in step 1123 of FIG. 11B, so that the condition may be satisfied if and only if the current smallest value is smaller than a threshold.

It should be noted that the flowchart of a process for removing the Gibbs artifact from an image described above is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure. For example, step 1102, step 1105, step 1108, step 1111, step 1114, step 1117, step 1120, step 1123 and step 1126 may be performed sequentially at an order other than that described above in FIG. 11B. At least two steps of step 1102, step 1105, step 1108, step 1111, step 1114, step 1117, step 1120, step 1123 and step 1126 may be performed concurrently. Step 1102, step 1105, step 1108, step 1111, step 1114, step 1117, step 1120, step 1123 and step 1126 may be merged into a single step or divided into a number of steps. In addition, one or more other operations may be performed before/after or in performing step 1102, step 1105, step 1108, step 1111, step 1114, step 1117, step 1120, step 1123 and step 1126. At least one of step 1102, step 1105, step 1108, step 1111, step 1114, step 1117, step 1120, step 1123 and step 1126 may be unnecessary and may be omitted.

Figure 11C:
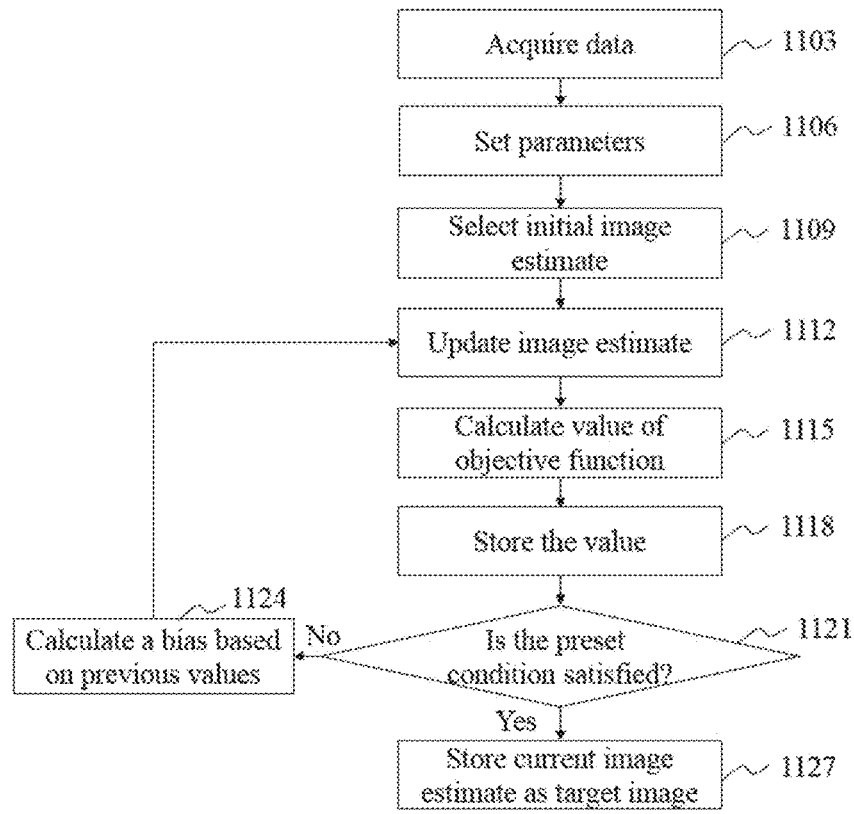

FIG. 11C illustrates a further exemplary flowchart for a process of an image reconstruction according to some embodiments of the present disclosure. Step 1103, step 1106, step 1109, step 1112, and step 1115 may be the same as those of FIG. 11A.

After the value of the objective function is calculated in step 1115, the value may be stored in the storage unit 430 in step 1118. In some embodiments, only a single value of the objective function may be stored so that the value in each iteration may replace the value stored in the previous iteration. In some embodiments, a plurality of values of the objective function from a plurality of iterations may be stored. A determination in step 1121 may be performed as to whether the condition is satisfied as described before in FIG. 11A and FIG. 11B. If the condition is satisfied, the current image may be saved as the target image in step 1127, the image may then be output as the final image. If the condition is not satisfied, a contribution factor, or bias, may be calculated based on the previous value(s) stored in step 1124. The contribution factor may represent how the previous value(s) in one or more previous iterations contribute to the image in the current iteration. The contribution factor may be calculated from the value in the previous iteration or may be calculated from a plurality of values of the objective function from a plurality of iterations based on the values stored in step 1118.

In some embodiments, the contribution factor may be calculated by a machine learning method. According to the machine learning method, the algorithm in calculating the contribution factor may be updated based on the magnitude and/or amount of the values stored in step 1118.

After calculating the contribution factor, or bias, in step 1124 the image may be updated based on the calculated contribution factor and the similar process may follow until the preset condition is satisfied. And the image satisfying the condition may then be output as the final image.

In some embodiments, the process may include applying an algorithm to perform the iteration process as described in FIG. 11A, FIG. 11B, and/or FIG. 11C. The algorithm may include but not limit to a recursion, a nonlinear conjugate gradient method, a bisection method, an exhaustive search (or brute-force search), a greedy algorithm, a divide and conquer algorithm, a dynamic programming method, an iterative method, a branch-and-bound algorithm, a backtracking algorithm, or the like, or any combination thereof.

It should be noted that the above descriptions of the image reconstruction processes are provided for the purposes of illustration, not intended to limit the scope of the present disclosure. For persons having ordinary skills in the art, various variations and modifications may be conducted under the teaching of the present disclosure. However, those variations and modifications may not depart the protecting scope of the present disclosure. It should be appreciated for those skilled in the art that the process described in FIG. 11B, and FIG. 11C may be combined to form a process which store both the current smallest value of the objective function and value in a plurality of previous iterations. Accordingly, the image may be updated by the contribution factor calculated from values in a plurality of previous iterations and the preset condition may be determined by the current smallest value.

In some embodiments, the present image reconstructing process may be used in data relating to various types of subjects including but not limiting to a head, a breast, a lung, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof. In some embodiments, the image reconstructing process may include a plurality of configurations, wherein each configuration may specifically be used in processing an image of a single type of subject. In some embodiments, the configuration may be used in processing the images of a plurality of subjects.

As described elsewhere in the present disclosure, the image reconstructing process may include steps of low pass filtering, padding (e.g., zero padding), frequency analysis, and iterative image reconstruction. In some embodiments, the configuration described before may include a selection of low pass filters, a selection of size of the region where padding is applied, a division of data values for the application of a constraint in the k-space, a selection of objective function, or the like, or a combination thereof.

Figure 12A:
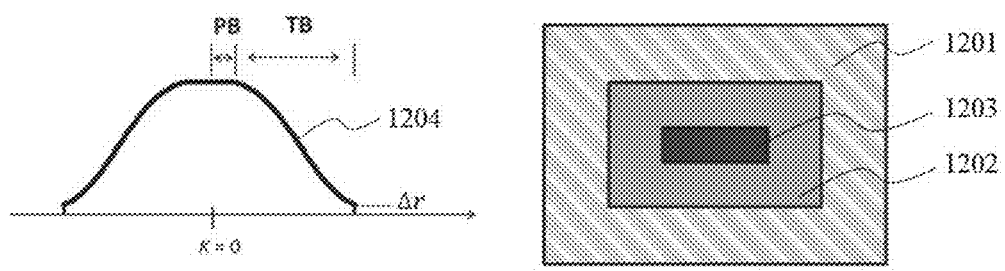
FIG. 12A and FIG. 12B illustrate two exemplary configurations in processing images of different subjects or different sections of the same subject in an image reconstructing process according to some embodiments of the present disclosure.
Figure 12B:
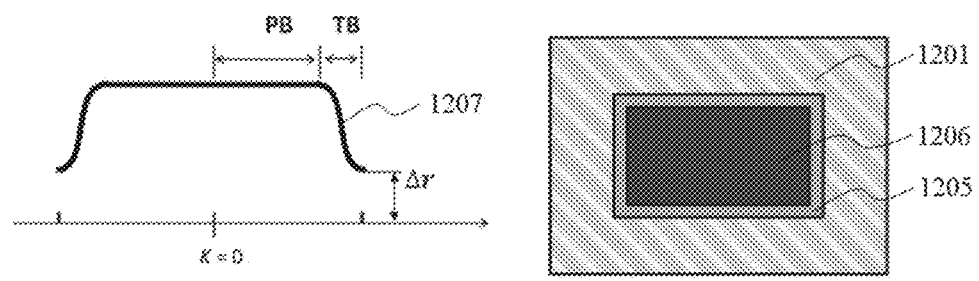

FIG. 12A and FIG. 12B illustrate two exemplary configurations in processing images of different subjects or different sections of the same subject in an image reconstructing process. In some embodiments, FIG. 12A illustrates an exemplary configuration with strong low pass filtering and strong iterative reconstruction. In some embodiments, FIG. 12B illustrates an exemplary configuration with a weak low pass filtering and a weak iterative reconstruction.

As shown in FIG. 12A and FIG. 12B, the low pass filter 1204 and 1207 may each include a passband (referred to as PB in the figure), a transition band (referred to as TB in the figure), and a threshold (referred to as $\Delta r$ in the figure). In some embodiments, the passband may be the region of frequency that is not filtered and/or attenuated (e.g., subject to a filter of zero strength), the stopband (not shown in the figure) may be the region of frequency that is mostly filtered and/or attenuated (e.g., subject to a filter of the highest strength compared to the passband and the transition band), and transition band may be the region between the passband and the stopband subject to an intermediate filtering and/or attenuation (e.g., subject to a filter of an intermediate strength compared to the passband and the stopband). In some embodiments, the threshold may indicate the highest amplitude that the oscillatory tail in the stopband, referred to as a ripple in the stopband (also referred to as a stopband ripple) may reach.

The filter 1204, as illustrated in FIG. 12A, may include a narrow passband, a wide transition band, and a low threshold $\Delta r$. As used herein, a low threshold $\Delta r$ may indicate that the threshold is less than a characteristic percentage of the normalized amplitude of the frequency characteristic curve. For example, the characteristic percentage may be 20% or less. As another example, the characteristic value may be 30% or less. As used herein, a narrow band may indicate that the band is less than or equal to a specific threshold. For example, the specific threshold may be 30% or less of (TB+PB+SB), i.e., the summation of transition band, Pass band, and Stop band. As another example, the specific threshold may be 20% or less of (TB+PB+SB). As used herein, a wide band may indicate that the band is larger than or equal to a threshold. For example, the threshold may be 70% or more of (TB+PB+SB), i.e., the summation of transition band, Pass band, and Stop band. As another example, the threshold may be 80% or more of (TB+PB+SB). This configuration may indicate that only a small range of frequencies may remain unfiltered in the PB, while a large range of frequencies may be filtered in a TB. It may also indicate that frequencies higher than the TB may be heavily filtered and attenuated to a low amplitude indicated by $\Delta r$.

Referring now to FIG. 12B, the filter 1207 may include a wide passband, a narrow transition band and a threshold $\Delta r$ of high range, for example 30% to 50%, of the normalized amplitude of the frequency characteristic curve. This configuration may indicate a large range of frequencies may remain unfiltered in the PB, while a small range of frequencies may be filtered in the TB. It may also indicate that frequencies higher than TB may be moderately filtered and attenuated to a medium amplitude indicated by $\Delta r$.

FIG. 12A and FIG. 12B also illustrate two exemplary configurations of the division of ranges of frequencies and the selection of objective functions in the k-space (also referred to as the frequency range). According to some embodiments of the present disclosure, the k-space may be divided into several ranges of frequencies.

In some embodiments, as shown in FIG. 12A and FIG. 12B, 1201 may represent a padded region, region 1202 and region 1205 may each represent a region that may be modified during the iterative reconstruction, while region 1203 and region 1206 may each represent a region that either may not be modified or may only be slightly modified during the iterative reconstruction. In some embodiments, region 1201 may correspond to region 1001 in FIG. 10A or FIG. 10B. In some embodiments, region 1202 or region 1205 may correspond to region 1004 in FIG. 10B, while region 1203 or region 1206 may correspond to region 1003 in FIG. 10A.

In some embodiments, region 1202 or region 1205, together with region 1201 may be correspond to D1 in formula (1) and (2), while region 1203 or region 1206 may correspond to D2 in formula (1) and (2).

Referring back to FIG. 12A, in which region 1202 is larger than region 1203, the data of a large region of frequencies may be modified during the iterative reconstruction (also referred to as strong iterative reconstruction).

As shown in the FIG. 12B, in which region 1205 is smaller than region 1206, the data of a small region of frequency may be modified during the iterative reconstruction (also referred to as weak iterative reconstruction).

In some embodiments, the configuration described in FIG. 12A may be used in processing an image with high Gibbs artifacts. In some embodiments, the configuration described in FIG. 12b may be used in processing an image with low Gibbs artifacts.

This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments. It should be appreciated for those skilled in the art that the configuration described in FIG. 12A and FIG. 12B may be combined arbitrarily. Merely by way of example, it should be obvious to those skilled in the art to combine the weak filtering in FIG. 12A with the strong iterative reconstruction in FIG. 12B, vice versa. It should also be obvious to those skilled in the art to, for example, select or design a filter with narrow TB and wide PB as described in FIG. 12B but with a low threshold as described in FIG. 12A.

Figure 13:
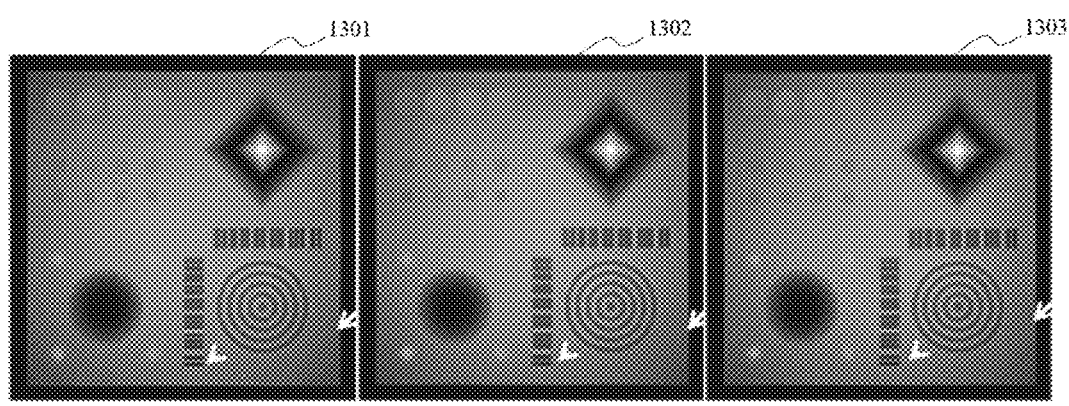
FIG. 13 illustrates three exemplary images generated from water phantom scanning and different processing steps according to some embodiments of the present disclosure.

FIG. 13 illustrates three exemplary images generated from water phantom scanning and different processing steps according to some embodiments of the present disclosure. In some embodiments, water phantom with different water mold textures, shapes and other conditions were used for scanning, and water phantom scanning was performed for examining the effectiveness of the data processing system. Images 1301, 1302, and 1303 were based on the same data array acquired from the same water phantom scanning.

The image 1301 was generated through a data processing protocol excluding filtering. Specifically, the size of the data array in the k-space was doubled through zero-padding outside of the natural region of the data in the k-space. Then an image was constructed through an inverse Fourier transform of the data in both the natural region and the padded region in the k-space. An exemplary image constructed according to this zero-padding protocol is shown in the image 1301.

The image 1302 was generated through a data processing protocol including filtering. Specifically, the data were filtered through a low-pass filter having a Hanning window in the transition band with a normalized transition bandwidth of 0.2 and a Δr of 0.2. The size of the filtered data array in the k-space was doubled through zero-padding outside the natural region of the data in the k-space. Then an image was constructed through an inverse Fourier transform of the filtered data in the natural region and the data in the padded region. An exemplary image constructed according to this traditional low-pass filtering protocol is shown as the image 1302.

The image 1303 was generated through a data processing protocol including low-pass filtering, zero-padding, and total variation reconstruction, as described in the present disclosure. Specifically, the data were filtered through a low-pass filter having a Hanning window in the transition band with a normalized transition bandwidth of 0.25 and a Δr of 0.65. The size of the filtered data array in the k-space was doubled through zero-padding outside the natural region of the data in k-space. Then a total variation reconstruction was performed. In the total variation reconstruction, a function as shown in Equation (4) was used as the objective function and a function as shown in Equation (5) was used as the constraint. The parameter Ai was set as 0.005, the parameter $\lambda_2$ was set as 0.0015, the parameter $P_2$ was a matrix used to choose a region $D_2$ in which the frequency of data were no larger than the highest frequency of the original data multiplied by 0.75, and the parameter $P_1$ was a matrix used to choose the remaining region $D_1$ other than $D_2$. The total variation reconstruction process included a plurality of iterations. During the iteration, steps 1103 to 1107 in FIG. 11A, FIG. 11B, or FIG. 11C may be performed for minimizing the objective function. An exemplary target image representing the minimization of the objective function is shown in the image 1303.

In comparison with the images 1302 and 1303, the Gibbs artifacts in image 1301 are significant. For example, alternating bright and dark lines or bands (see arrows in 1301) may be present next to the border of an abrupt intensity change, regardless of the shape of the water phantom.

In image 1302, Gibbs artifacts may be reduced substantially through traditional low-pass filtering. For example, the numbers of the alternating bright and dark lines were reduced; the intensity of the artifact lines were weakened (see arrows in 1302). However, there were still some residual artifacts at the border of an abrupt intensity change, and the clarity of the image was deteriorated, especially for the detail structure at the borders. It may be indicated that the traditional low-pass filter may be effective in reducing Gibbs artifacts to some extent, but at the expense of lowered image clarity.

In image 1303, Gibbs artifacts were reduced through image reconstruction involving low-pass filtering and total variation. For example, the alternating bright and dark lines were greatly removed and became essentially invisible; the details of the structures at the border of an abrupt intensity change retained (see arrows in 1303). It may be indicated that the low-pass filtering in the present disclosure combined with the total variation reconstruction process may be effective in removing Gibbs artifacts and retaining the detailed structures or the clarity of the image.

Figure 14:
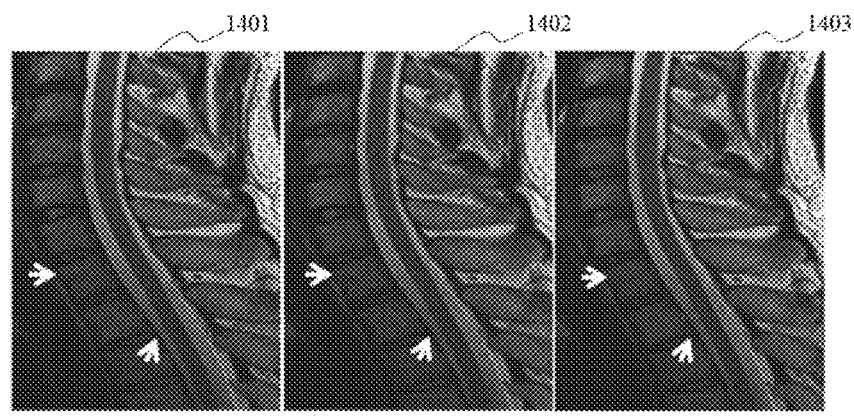
FIG. 14 illustrates three exemplary images generated from C-spine scanning and different processing steps according to some embodiments of the present disclosure.

FIG. 14 illustrates three exemplary images generated from cervical spine (C-spine) scanning and different processing steps according to some embodiments of the present disclosure. Images 1401, 1402, and 1403 were based on the same data array acquired from the same C-spine scanning.

The image 1401 was generated through a data processing protocol excluding filtering. The processing procedure and parameters used in the processing were the same with that of image 1301. For example, the size of the data array was doubled after zero-padding.

The image 1402 was generated through a data processing protocol including filtering. The processing procedure and parameters used in the processing were the same with that of image 1302. For example, a low-pass filter which having a Hanning window in the transition band with a normalized transition bandwidth of 0.2 and a Δr of 0.2 was used.

The image 1403 was generated through a data processing protocol including low-pass filtering, zero-padding, and total variation reconstruction, as described in the present disclosure. The processing procedure and parameters used in the processing were the same with that of image 1303. For example, a low-pass filter having a Hanning window in the transition band with a normalized transition bandwidth of 0.25 and a Δr of 0.65 was used, the parameter $\lambda_1$ was set as 0.005, the parameter $\lambda_2$ was set as 0.0015, and the parameter $P_2$ was a matrix used to choose a region $M_2$ in which the frequency of data were no larger than the highest frequency of the original data multiplied by 0.75.

Similarly with images 1301, 1302, and 1303, the image 1401 has significant Gibbs artifacts (see arrows in 1401); the image 1402 has substantially reduced Gibbs artifacts but with residual artifacts and blurred border of an abrupt intensity change (see arrows in 1402); the image 1403 has significantly reduced Gibbs artifacts, and retained sharp and clear borders and detailed structures (see arrows in 1403), especially for the areas around the fatty tissue on the back of the neck. It may be determined that the low-pass filtering in the present disclosure combined with the total variation reconstruction process may be effective in removing Gibbs artifacts and retaining the detailed structures or the clarity of the image.

Figure 15:
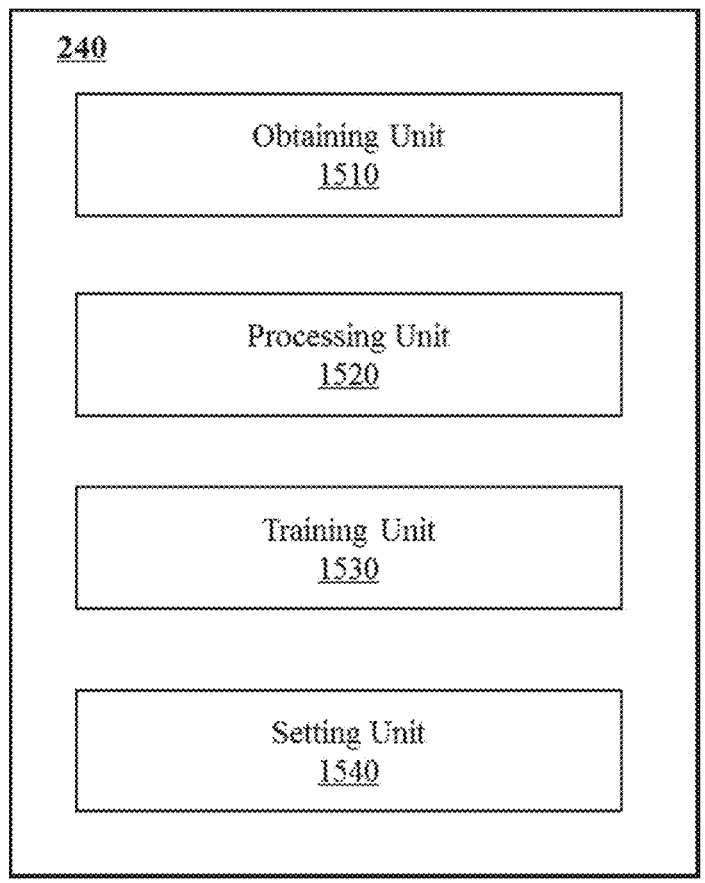
FIG. 15 is a block diagram illustrating an exemplary processing module according to some embodiments of the present disclosure.

FIG. 15 is a block diagram illustrating an exemplary processing module according to some embodiments of the present disclosure. The processing module 240 may include an obtaining unit 1510, a processing unit 1520, a training unit 1530, and a setting unit 1540.

The obtaining unit 1510 may be configured to obtain data and/or information associated with the image processing system 200. For example, the obtaining unit 1510 may obtain one or more sets of image data. In some embodiments, a set of image data may include a data array in k-space (also referred to as the frequency domain) or a data array in an image domain (also referred to as space domain). As another example, the obtaining unit 1510 may obtain one or more weight matrices corresponding to the sets of image data. As a further example, the obtaining unit 1510 may obtain one or more preliminary machine learning models for model training. As still another example, the obtaining unit 1510 may obtain a plurality of training data. More descriptions of the training data may be found elsewhere in the present disclosure (e.g., FIG. 17 and the descriptions thereof).

The processing unit 1520 may be configured to process data and/or information associated with the image processing system 200. In some embodiments, the processing unit 1520 may process a first set of image data based on a first trained machine learning model, to generate a second set of image data. In some embodiments, the second set of image data may have a relatively high resolution and/or a relatively low level of artifacts with respect to the first set of image data. In some embodiments, the processing unit 1520 may perform a weighted fusion on a first set of image data and a second set of image data, to generate a target set of image data (e.g., a target image). In some embodiments, the processing unit 1520 may process a set of image data (e.g., a first set of image data, a second set of image data, and/or a target set of image data). For example, the processing unit 1520 may perform a low pass filtering on the first set of image data. As another example, the processing unit 1520 may process a plurality of sets of input image data and/or a plurality of sets of expected image data to generate training data of the preliminary machine learning model. As still another example, the processing unit 1520 may perform an inverse Fourier transform to transform a data array in k-space (e.g., the target set of image data) to a data array in an image domain (e.g., a target image). As still another example, the processing unit 1520 may perform a Fourier transform to transform a data array in an image domain to a data array in k-space.

The training unit 1530 may be configured to determine one or more trained machine learning models by training one or more preliminary machine learning models. The trained machine learning model may be configured to generate a second set of image data with a relatively high resolution and/or a relatively low level of artifacts based on a first set of image data with a relatively low resolution and/or a relatively high level of artifacts. For example, the training unit 1530 may train the preliminary machine learning model based on a plurality of sets of input image data and a plurality of sets of expected image data. More descriptions of the determination of the trained machine learning model may be found elsewhere in the present disclosure (e.g., FIG. 17, and descriptions thereof). In some embodiments, the training unit 1530 may further update one or more trained machine learning models based on other training data (e.g., the training data that are not used in the training of the preliminary machine learning models, processing results that are generated in the usage of the trained machine learning models).

The setting unit 1540 may be configured to set k-space. In some embodiments, the setting unit 1540 may set the k-space as a first part and a second part. The first part may include the k-space center (or the k-space central region). In some embodiments, the setting unit 1540 may further set the first part as a first region and a second region. The second region may include the k-space center.

The units in the processing module 240 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the units may be combined into a single unit, and any one of the units may be divided into two or more blocks. For example, the processing unit 1520 and the setting unit 1540 may be combined into a single unit. As another example, the training unit 1530 may be omitted, and the trained machine learning model may be obtained from a storage device (e.g., the storage module 220) of the image processing system 200 or an external storage device. As a further example, the processing module 240 may include a storage unit (not shown) used to store information and/or data (e.g., the first set of image data, the second set of image data, the trained machine learning model) associated with the image processing system 200.

Figure 16:
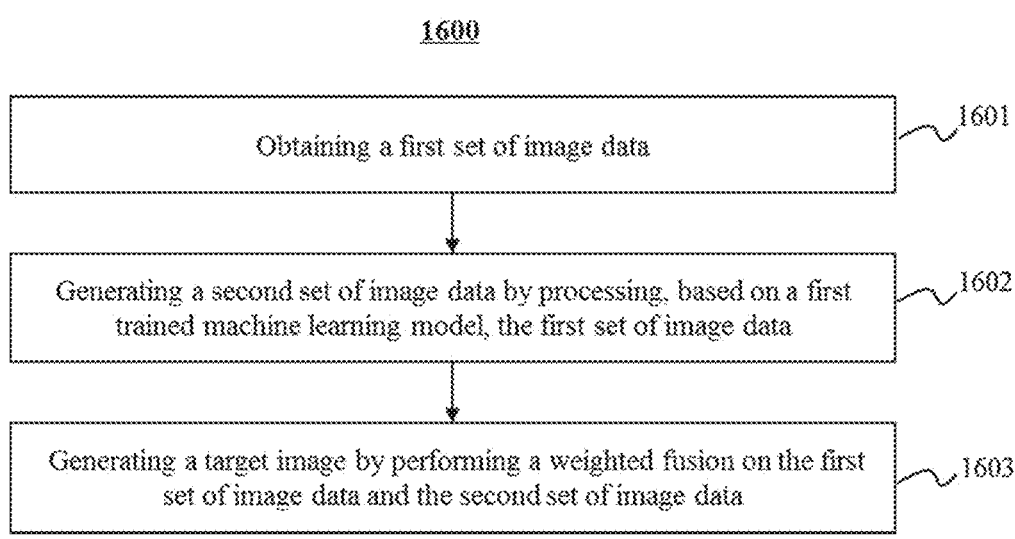
FIG. 16 is a flowchart illustrating an exemplary process for generating a target image according to some embodiments of the present disclosure.

FIG. 16 is a flowchart illustrating an exemplary process for generating a target image according to some embodiments of the present disclosure. The process 1600 may be executed by the data processing system 150 or the image processing system 200. For example, the process 1600 may be implemented as a set of instructions stored in the storage module 220. In some embodiments, one or more units in FIG. 15 may execute the set of instructions, and when executing the instructions, the unit(s) may be configured to perform the process 1600. The operations of the illustrated process presented below are intended to be illustrative. In some embodiments, the process 1600 may be accomplished with one or more additional operations not described and/or without one or more of the operations discussed. Additionally, the order in which the operations of the process 1600 illustrated in FIG. 16 and described below is not intended to be limiting.

In 1601, the processing module 240 (e.g., the obtaining unit 1510) may obtain a first set of image data.

In some embodiments, the first set of image data may be a data array (also referred to as a first data array). In some embodiments, the first set of image data may include a data array in k-space (also referred to as the frequency domain). In some embodiments, the first set of image data may include a data array in an image domain (also referred to as space domain). In some embodiments, the first set of image data may be associated with a scan of a subject. The subject may include a human being, an animal, or a portion thereof, as described in connection with operation 301. In some embodiments, the first set of image data may correspond to a first image of the subject.

In some embodiments, the processing module 240 may obtain the first set of image data based on k-space data generated by a magnetic resonance imaging (MRI) scanner (e.g., the MRI scanner 110). More descriptions of the generation of the k-space data may be found elsewhere in the present disclosure (e.g., FIG. 4 and descriptions thereof). For example, the processing module 240 may obtain the first set of image data by performing an inverse Fourier transform on the k-space data generated by the MRI scanner. As another example, the processing module 240 may obtain the first set of image data by collecting, using one or more reconstruction algorithms, the k-space data generated by the MRI scanner. The one or more image reconstruction algorithms may include a parallel imaging algorithm, a compressed sensing algorithm, a partial Fourier acquisition algorithm, a regridding algorithm, or the like, or any combination thereof.

In some embodiments, the processing module 240 may obtain the first set of image data by collecting k-space data along a Cartesian trajectory (e.g., a unidirectional parallel, circuitous parallel) or a non-Cartesian trajectory (e.g., spiral, radial, propeller, blade, or windmill). In some embodiments, the processing module 240 may obtain the first set of image data by performing a phase encoding and a frequency encoding on MRI signal obtained from the MRI scanner. In some embodiments, the processing module 240 may obtain the first set of image data from a storage device of the data processing system 150 or the image processing system 200, or an external storage device.

In some embodiments, the k-space data generated by the MRI scanner may be undersampled. For example, the first set of image data may include a region (e.g., region 1002 illustrated in FIG. 10A) including the k-space center (or the k-space central region) of the first set of image data, and a region (e.g., region 1001 illustrated in FIG. 10A) outside the k-space center of the first set of image data. The region (e.g., region 1002 illustrated in FIG. 10A) including the k-space center of the first set of image data may be filled with data obtained by scanning the subject. In some embodiments, the region (e.g., region 1001 illustrated in FIG. 10A) outside the k-space center of the first set of image data may be unfilled. As another example, the first set of image data may include a region (e.g., region 1003 illustrated in FIG. 10B) including the k-space center of the first set of image data, and multiple regions (e.g., region 1004 illustrated in FIG. 10B, region 1001 illustrated in FIG. 10B) outside the k-space center of the first set of image data. The region (e.g., region 1003 illustrated in FIG. 10B) including the k-space center of the first set of image data may be filled with data obtained by scanning the subject. In some embodiments, the region (e.g., region 1004 illustrated in FIG. 10B) outside the k-space center of the first set of image data may be partially filled with data obtained by scanning the subject. In some embodiments, the region (e.g., region 1001 illustrated in FIG. 10B) outside the k-space center of the first set of image data may be unfilled. Accordingly, the filled data values in region 1003 and region 1004 may form a data matrix in k-space. In some embodiments, the k-space data may be obtained along a Cartesian sampling trajectory. In some embodiments, a k-space may be filled by 256 data encoding lines along a phase encoding direction (e.g., from −128 to +127). In some embodiments, the k-space (e.g., the k-spaces illustrated in FIGS. 10A and 10B) may not be completely filled. For example, ten data encoding lines along the phase encoding direction (e.g., from −5 to +4) may be completely filled in region 1003 corresponding to low frequency data of the first set of image data. As another example, data encoding lines along the phase encoding direction (e.g., from −100 to −6, and from +4 to +98) may be interlaced filled (acceleration rate R for interlaced filling may be 2) in region 1004. Region 1001 corresponding to high frequency data of the first set of image data may not be acquired along the phase encoding direction (e.g., from −128 to −101, from +99 to +127).

In some embodiments, the processing module 240 may recover unfilled data in the region (e.g., region 1004 illustrated in FIG. 10B) outside the k-space center of the first set of image data by fitting the filled data in this region. For example, the processing module 240 may recover the unfilled data in the region 1004 based on compressed sensing, sensitivity encoding (SENSE), simultaneous acquisition of spatial harmonics (SMASH), generalized autocalibrating partially parallel acquisitions (GRAPPA), AUTO-SMASH, variable-density (VD)-AUTO-SMASH, generalized SMASH, mSMASH, partially parallel imaging with localized sensitivities (PILS), sensitivity profiles from an array of coils for encoding and reconstruction in parallel (SPACE RIP), or the like, or any combination thereof. In some embodiments, the processing module 240 may perform a padding (e.g., a zero padding, a non-zero padding) on the region (e.g., region 1001 illustrated in FIGS. 10A and 10B) outside the k-space center of the first set of image data. In some embodiments, using the first set of image data obtained in this way, a mosaic effect may be reduced in subsequent processing.

In 1602, the processing module 240 (e.g., the processing unit 1520) may generate a second set of image data. In some embodiments, the processing module 240 may generate the second set of image data by processing, based on a first trained machine learning model, the first set of image data.

In some embodiments, the second set of image data may be a data array (also referred to as a second data array). In some embodiments, the second set of image data may include a data array in k-space. In some embodiments, the second set of image data may include a data array in an image domain. In some embodiments, the second set of image data may correspond to a second image of the subject. In some embodiments, the second set of image data (or the second image) may have a relatively high resolution and/or a relatively low level of artifacts with respect to the first set of image data (or the first image).

In some embodiments, the processing module 240 may generate the second set of image data based on the first set of image data according to the first trained machine learning model. The first trained machine learning model may be determined by training a first machine learning model. The first machine learning model may include one or more algorithms used for generating an output result (e.g., the second set of image data) based on input image data (e.g., the first set of image data). In some embodiments, the first machine learning model may be a neural network model. In some embodiments, the neural network model may include an artificial neural network (ANN), a convolutional neural network (CNN), a generative adversarial network (GAN), or the like, or any combination thereof. In some embodiments, the first machine learning model may be a deep learning model. In some embodiments, the deep learning model may include one or more deep neural networks (DNN), one or more deep Boltzmann machines (DBM), one or more stacked auto encoders, one or more deep stacking networks (DSN), etc.

Figure 20:
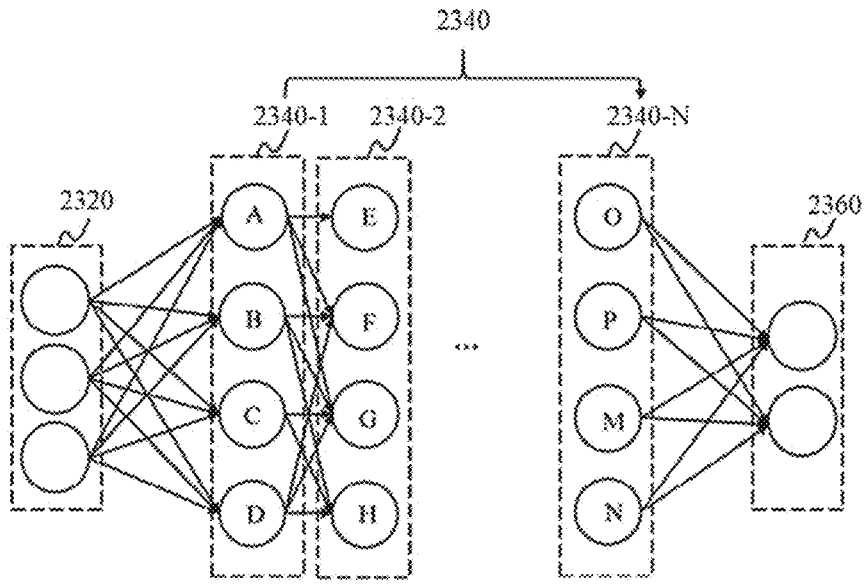
FIG. 20 is a schematic diagram illustrating a machine learning model according to some embodiments of the present disclosure.

In some embodiments, the first machine learning model may include a multi-layer structure, as illustrated in FIG. 20. For example, the first machine learning model may include an input layer 2320, an output layer 2360, and one or more hidden layers 2340 between the input layer 2320 and the output layer 2360. In some embodiments, the hidden layers 2340 may include one or more convolution layers 2340-1, one or more rectified-linear unit layers (ReLU layers), one or more pooling layers 2340-2, one or more fully connected layers 2340-N, or the like, or any combination thereof. As used herein, a layer of a model may refer to an algorithm or a function for processing input data of the layer. Different layers may preform different kinds of processing on their respective input. A successive layer may use output data from a previous layer of the successive layer as input data. In some embodiments, each of the layer may include one or more nodes. In some embodiments, each node may be connected to one or more nodes in a previous layer. The number of nodes in each layer may be the same or different. In some embodiments, each node may correspond to an activation function. As used herein, an activation function of a node may define an output of the node given an input or a set of inputs. In some embodiments, each connection between two of the plurality of nodes in the first machine learning model may transmit a signal from one node to another node. In some embodiments, each connection may correspond to a weight. As used herein, a weight corresponding to a connection may be used to increase or decrease the strength of the signal at the connection.

The first trained machine learning model may refer to a machine learning model that has been trained using training data (e.g., a plurality of first sets of input image data, a plurality of first sets of expected image data). The first trained machine learning model may include one or more relatively optimized parameters relating to the algorithms (e.g., the CNN) of the first machine learning model, so that the sufficiency and/or accuracy of artifact removal based on the first trained machine learning model may be satisfactory for practical use. In some embodiments, the processing module 240 (e.g., the training unit 1530) may determine the first trained machine learning model by training, based on training data, the first machine learning model. In some embodiments, the processing module 240 may make the first machine learning model learn one or more features of the training data and adjust one or more layers (or one or more parameters) of the multi-layer structure.

In some embodiments, the first trained machine learning model may be generated by one or more other processors inside and/or outside the data processing system 150 or the image processing system 200. In some embodiments, the processing module 240 may directly obtain the first trained machine learning model, e.g., from the storage module 220. More descriptions of the determination of the first trained machine learning model may be found elsewhere in the present disclosure (e.g., FIG. 17 and descriptions thereof). In some embodiments, the first trained machine learning model may be a previously-trained machine learning model that is trained with relatively low quality image data and relatively high quality image data. In some embodiments, the relatively low quality image data may include more Gibbs artifacts, while the relatively high quality image data may include less Gibbs artifacts. In some embodiments, the first trained machine learning model may be a previously-trained machine learning model that is trained with k space filled with less high spatial frequency data and k space filled with more high spatial frequency data.

In 1603, the processing module 240 (e.g., the processing unit 1520) may generate a target image by performing a weighted fusion on the first set of image data and the second set of image data.

As used herein, "a weighted fusion between the first set of image data and the second set of image data" may refer to a process of combining one or more data values in the k-space of the first set of image data and one or more data values in the k-space of the second set of image data according to one or more corresponding weighting factors. For example, the processing module 240 may determine a first weight matrix corresponding to the first set of image data, and a second weight matrix corresponding to the second set of image data. The processing module 240 may generate the target image by performing, according to the first weight matrix and the second weight matrix, a weighted sum of the first set of image data and the second set of image data in k-space. More descriptions of the generation of the target image may be found elsewhere in the present disclosure (e.g., FIG. 18 and descriptions thereof). In some embodiments, "a weighted fusion between the first set of image data and the second set of image data" may also refer to a synthesis of the first set of image data and the second set of image data.

In some embodiments, partial or all of the unfilled data along the phase encoding direction (e.g., from −128 to −101, from +99 to +127) in region 1001 may be recovered. In some embodiments, data values in region 1002, region 1003, and/or region 1004 may remain unchanged (i.e., not changed in the weighted fusion process compared to their respective original values before the weighted fusion) when the weighted fusion is performed on the first set of image data and the second set of image data. In some embodiments, a changing extent of data values in region 1002, region 1003, and/or region 1004 may be less than a changing extent of data values in the region 1001 when the weighted fusion is performed on the first set of image data and the second set of image data.

Although the artifacts in the second set of image data may be effectively suppressed, and the mosaic effect may be reduced to some extent, in some embodiments, problems such as weakening of the structural features of the subject and an increase in the signal to noise ratio may occur in the second set of image data. In order to obtain an MRI image with more realistic data and more natural display effect, the processing module 240 may perform the weighted fusion on the first set of image data and the second set of image data by combining the first set of image data with better structure feature of the subject and smaller signal to noise ratio, with the second set of image data with better artifact correction effect. Because data in the region including the k-space center (or the k-space central region) correspond to the structural features associated with the subject, and data in the region outside the k-space center (especially the high-frequency component) correspond to detailed features associated with the subject, it is necessary to ensure that the data used in weighted fusion operation is the data in the k-space.

As described in the present disclosure, the second set of image data may be generated by performing an artifact correction on the first set of image data with a relatively low resolution and/or a relatively high level of artifacts based on the first trained machine learning model. The degree of suppression of truncation artifacts may be increased without increasing the scanning time. The target image may be determined by performing a weighted fusion on the first set of image data with a relatively low resolution and/or a relatively high level of artifacts and the second set of image data with a relatively high resolution and/or a relatively low level of artifacts. The target image may include one or more data values in the first set of image data and one or more data values in the second set of image data. Accordingly, the target image (e.g., an MRI image) with better artifact correction effect may be determined, and the resolution and the signal to noise ratio of the target image may be substantially unaffected after the artifact correction.

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added elsewhere in the process 1600. In some embodiments, an operation for preprocessing the first set of image data may be added before operation 1602 and/or operation 1603. For example, a rectifying procedure may be performed to correct or remove unreliable and incorrect data. As another example, a noise filtering procedure may be performed to remove the noise produced during the scanning process. As still another example, a filter (e.g., a low pass filtering) may be implemented to remove data in undesired frequency ranges (e.g., data in high-frequency ranges). As still another example, the first set of data may be padded (for example, zero-padded) to reduce mosaic effect according to some embodiments of present disclosure. As still another example, the processing module 240 may perform an image normalization, an image segmentation, an image smoothing, or the like, or any combination thereof on the first set of image data. As a further example, the processing module 240 may perform one or more operations illustrated in FIGS. 3, 7, 11A, 11B, and/or 110. In some embodiments, the data of the first set of image data may be classified into several regions based on their frequencies, and different procedures may be performed on data in different frequency ranges.

Figure 17:
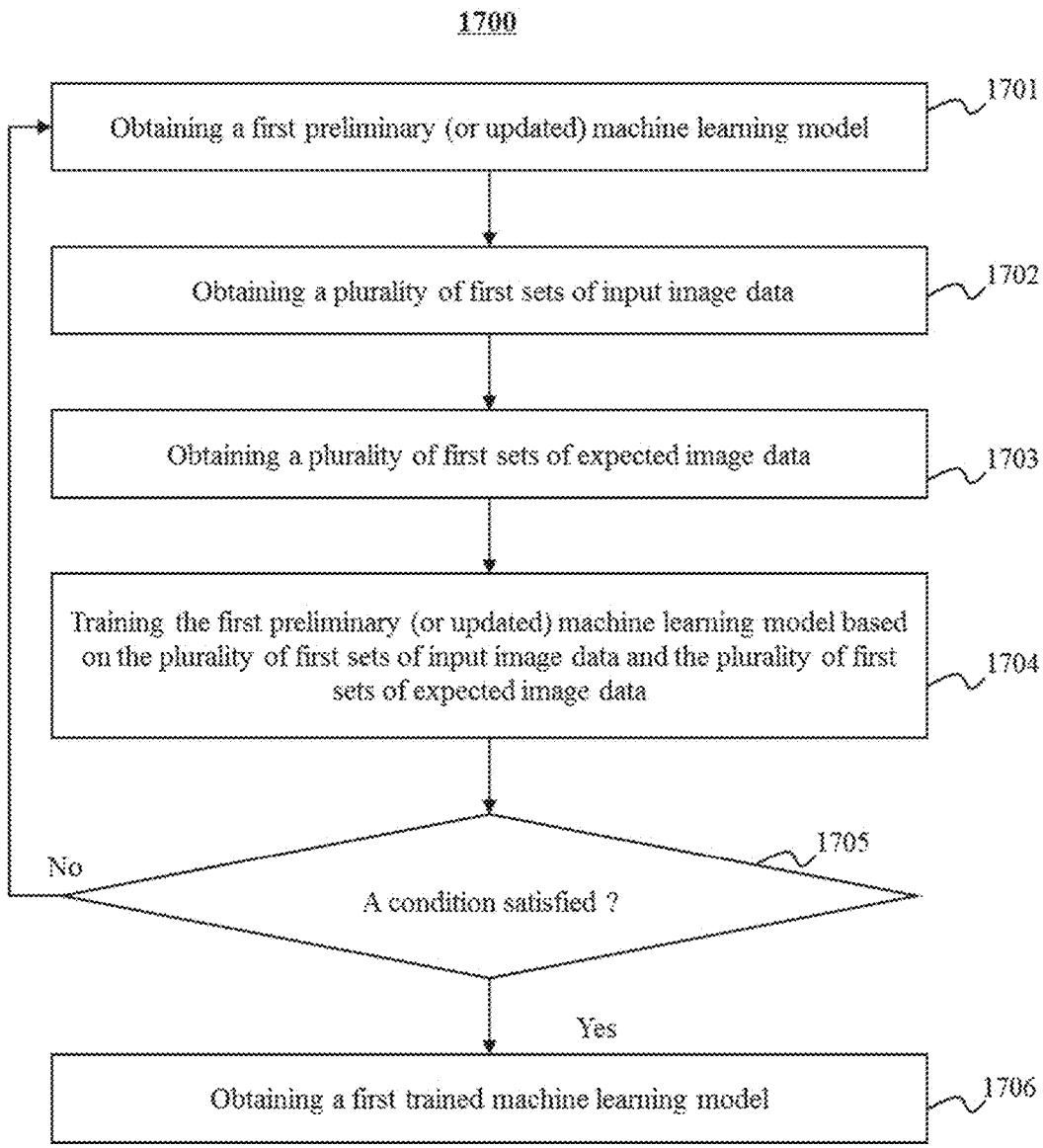
FIG. 17 is a flowchart illustrating an exemplary process for obtaining a first trained machine learning model according to some embodiments of the present disclosure.

FIG. 17 is a flowchart illustrating an exemplary process for obtaining a first trained machine learning model according to some embodiments of the present disclosure. The process 1700 may be executed by the data processing system 150 or the image processing system 200. For example, the process 1700 may be implemented as a set of instructions stored in the storage module 220. In some embodiments, one or more units in FIG. 15 may execute the set of instructions, and when executing the instructions, the unit(s) may be configured to perform the process 1700. The operations of the illustrated process presented below are intended to be illustrative. In some embodiments, the process 1700 may be accomplished with one or more additional operations not described and/or without one or more of the operations discussed. Additionally, the order in which the operations of the process 1700 illustrated in FIG. 17 and described below is not intended to be limiting.

In 1701, the processing module 240 (e.g., the obtaining unit 1510) may obtain a first preliminary machine learning model.

The first preliminary machine learning model may refer to a machine learning model to be trained. The first preliminary machine learning model may include one or more model parameters. In some embodiments, the model parameter(s) may have one or more initial values. In some embodiments, the initial values of the model parameter(s) may be default values determined by the data processing system 150 (or the image processing system 200) or preset by a user or operator of the data processing system 150 (or the image processing system 200).

In some embodiments, the obtaining unit 1510 may obtain the first preliminary machine learning model from a storage device (e.g., the storage module 220) disclosed elsewhere in the present disclosure and/or an external data source (not shown).

In 1702, the processing module 240 (e.g., the obtaining unit 1510) may obtain a plurality of first sets of input image data. In some embodiments, each first set of input image data of the plurality of first sets of input image data may include a data array in k-space or a data array in an image domain. In some embodiments, the plurality of first sets of input image data may include a plurality of data arrays in k-space and/or a plurality of data arrays in an image domain.

In 1703, the processing module 240 (e.g., the obtaining unit 1510) may obtain a plurality of first sets of expected image data. In some embodiments, each first set of expected image data of the plurality of first sets of expected image data may include a data array in k-space or a data array in the image domain. In some embodiments, the plurality of first sets of expected image data may include a plurality of data arrays in k-space and/or a plurality of data arrays in an image domain.

In some embodiments, each first set of input image data may correspond to an image of the subject, and each first set of expected image data may correspond to another image of the subject. In some embodiments, each first set of input image data of the plurality of first sets of input image data may correspond to a first set of expected image data of the plurality of first sets of expected image data. In some embodiments, the each first set of input image data may have a relatively low resolution and/or a relatively high level of artifacts with respect to the corresponding first set of expected image data. In some embodiments, the each first set of expected image data may have more information of high frequency component in k-space with respect to the corresponding first set of input image data. In some embodiments, the artifacts may include a Gibbs artifact, a motion artifact, a flow artifact, a metal artifact, a chemical shift artifact, a partial volume artifact, wrap around artifact, or the like, or any combination thereof. In some embodiments, at least one of the first sets of expected image data may be generated by a magnetic resonance imaging (MRI) scanner, and/or may have a relatively high resolution and/or a relatively low level of artifacts.

In some embodiments, the processing module 240 may obtain one or more first sets of input image data of the plurality of first sets of input image data based on k-space data (within a first frequency range) generated by an MRI scanner (e.g., the MRI scanner 110). The processing module 240 may obtain the corresponding first sets of expected image data by processing the first sets of input image data. In some embodiments, the processing module 240 may reduce one or more artifacts in the first sets of input image data by processing, based on one or more processing algorithms, the first sets of input image data. In some embodiments, the one or more processing algorithms may include low-pass filtering in the k-space, interpolation in the k-space or image domain, total variation constrained data extrapolation, or the like, or any combination thereof. The processing module 240 may designate the first sets of processed input image data as the first sets of expected image data corresponding to the first sets of input image data.

In some embodiments, the processing module 240 may obtain one or more first sets of expected image data based on k-space data (within a second frequency range) generated by an MRI scanner (e.g., the MRI scanner 110). In some embodiments, the second frequency range may be larger than the first frequency range. The processing module 240 may obtain the corresponding first sets of input image data by processing the first sets of expected image data. In some embodiments, the k-space of a first set of expected image data may include a first part and a second part. The first part may include the k-space center (or the k-space central region). Data values in the first part may have a relatively low frequency, and data values in the second part may have a relatively high frequency. The processing module 240 may obtain the first sets of input image data corresponding to the first sets of expected image data by extracting a portion of the first sets of expected image data in the first part of the k-space. In some embodiments, the processing module 240 may further adjust the first sets of input image data. For example, the processing module 240 may perform a padding (e.g., a zero-padding) on the second part of the k-space with padded data. In some embodiments, the k-space of a set of expected image data may include a first part including the k-space central region and a second part outside of the first part. In some embodiments, the first part in the k-space of the set of expected image data may correspond to the first part in the k-space of a set of input image data, and the second part in the k-space of the set of expected image data may correspond to the second part in the k-space of the set of input image data.

In 1704, the processing module 240 (e.g., the training unit 1530) may train the first preliminary machine learning model based on the plurality of first sets of input image data and the plurality of first sets of expected image data.

In some embodiments, the processing module 240 may bring the plurality of first sets of input image data and the plurality of first sets of expected image data into the first preliminary machine learning model and train the first preliminary machine learning model. In some embodiments, the processing module 240 may perform one or more training processes until all the first sets of input image data and the corresponding first sets of expected image data are used for training. In some embodiments, the processing module 240 may generate an updated machine learning model in each training process. For example, the processing module 240 may bring one or more of the plurality of first sets of input image data and corresponding first sets of expected image data into the first preliminary machine learning model at one time for a first training process to generate a first updated machine learning model, and then the processing module 240 may bring one or more other first sets of input image data and corresponding first sets of expected image data into the first updated machine learning model at one time for a second training process to generate a second updated machine learning model. In some embodiments, one or more iterations of the training process may be performed until all the first sets of input image data and the corresponding first sets of expected image data are used for training, and a trained machine learning model may be obtained.

In a training process, the processing module 240 may process one or more of the plurality of first sets of input image data and corresponding first sets of expected image data in an initial layer of a machine learning model (e.g., the first preliminary or updated machine learning model), and the processing result may serve as input data for a next layer of the first preliminary or updated machine learning model. The processing module 240 may process input data of each layer of the first preliminary or updated machine learning model obtained from a previous layer. The processing module 240 may generate an output from a last layer of the first preliminary or updated machine learning model. The output generated from the last layer may include one or more updated model parameters relating to the machine learning model, one or more sets of output image data generated after one or more sets of input image data pass through all layers of the machine learning model, or the like. In some embodiments, the processing module 240 may compare a set of output image data to a first set of expected image data corresponding to a first set of input image data that generates the set of output image data. In some embodiments, the processing module 240 may update the model parameters of the first preliminary or updated machine learning model based on the result of the comparison to obtain a newly updated machine learning model, so that the newly updated machine learning model may be used to generate an output that is closer to the first set of expected image data than a previous machine learning model (e.g., the first preliminary or updated machine learning model).

In 1705, the processing module 240 (e.g., the training unit 1530) may determine whether a condition is satisfied.

The condition may relate to an iteration count representing the number of iterations that have been performed, a degree of change in model parameters updated in a current iteration comparing with those updated in a previous iteration, a difference between a set of output image data generated using the currently updated machine learning model and a corresponding first set of expected image data, or the like, or any combination thereof.

In response to a determination that the condition is satisfied (e.g., the iteration count is no less than a first threshold, the degree of change in model parameters between successive iterations is no more than a second threshold, or the difference between the output image data generated using the currently updated machine learning model and the corresponding first set of expected image data is less than a third threshold), the processing module 240 may execute the process 1700 to operation 1706. In response to a determination that the condition is not satisfied (e.g., the iteration count is less than the first threshold, the degree of change in model parameters between successive iterations is more than the second threshold, the difference between the output image data generated using the currently updated machine learning model and the corresponding first set of expected image data is no less than the third threshold), the processing module 240 may execute the process 1700 to operation 1701 to perform one or more iterations for further updating the updated machine learning model until the condition is satisfied.

In 1706, the processing module 240 (e.g., the training unit 1530) may obtain a first trained machine learning model.

In some embodiments, when the condition is satisfied, the processing module 240 may determine that the corresponding updated machine learning model obtained at the stopped iterative operation is trained well. The processing module 240 may assign the updated machine learning model as the trained machine learning model. The trained machine learning model may be configured to determine a second set of image data with a relatively high resolution and/or a relatively low level of artifacts, based on a first set of image data with a relatively low resolution and/or a relatively high level of artifacts, as described elsewhere in the present disclosure (e.g., FIG. 16, and descriptions thereof).

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, operation 1701 may be performed after operation 1702 and/or operation 1703. In some embodiments, operation 1705 may be omitted. In some embodiments, the first trained machine learning model may be further updated based on other training data (e.g., the training data that are not used in the training of the first preliminary machine learning model, processing results that are generated in the usage of the first trained machine learning model). In some embodiments, the updating of the first trained machine learning model may be performed at regular intervals.

Figure 18:
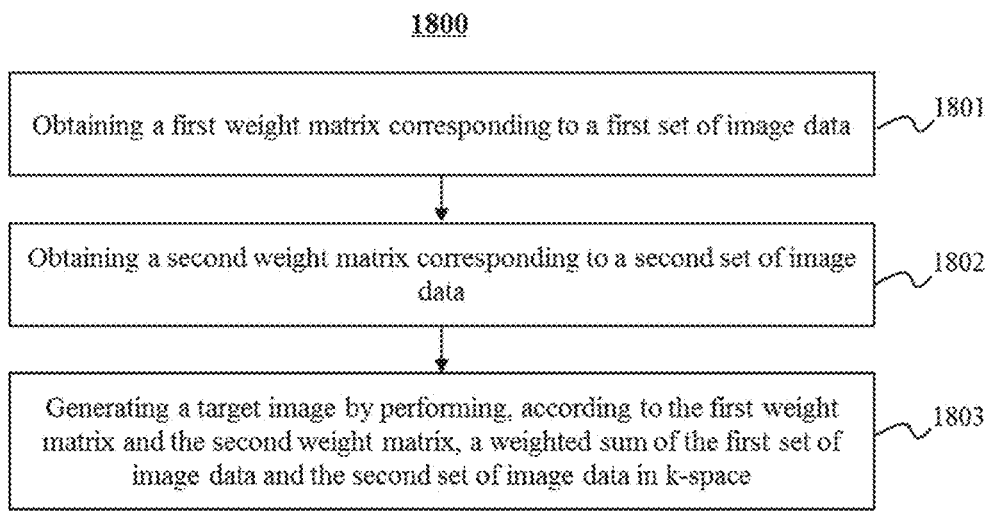
FIG. 18 is a flowchart illustrating an exemplary process for generating a target image according to some embodiments of the present disclosure.

FIG. 18 is a flowchart illustrating an exemplary process for generating a target image according to some embodiments of the present disclosure. The process 1800 may be executed by the data processing system 150 or the image processing system 200. For example, the process 1800 may be implemented as a set of instructions stored in the storage module 220. In some embodiments, one or more units in FIG. 15 may execute the set of instructions, and when executing the instructions, the unit(s) may be configured to perform the process 1800. The operations of the illustrated process presented below are intended to be illustrative. In some embodiments, the process 1800 may be accomplished with one or more additional operations not described and/or without one or more of the operations discussed. Additionally, the order in which the operations of the process 1800 illustrated in FIG. 18 and described below is not intended to be limiting. In some embodiments, operation 1603 illustrated in FIG. 16 may be performed according to the process 1800.

In 1801, the processing module 240 (e.g., the obtaining unit 1510) may obtain a first weight matrix corresponding to a first set of image data. In some embodiments, the size of the first weight matrix may be the same as the size of the first set of image data (or a first data array).

In some embodiments, the first weight matrix may include a first part and a second part. The first part may correspond to a region (e.g., the region 1002 or region 1003 illustrated in FIG. 10A) including the k-space center of the first set of image data. The first part may include a first set of weighting factors. In some embodiments, a weighting factor of the first set of weighting factors may correspond to a data value in the region including the k-space center of the first set of image data. The second part may correspond to a region (e.g., the region 1004 or the region 1001 illustrated in FIG. 10B) outside the k-space center of the first set of image data. The second part may include a second set of weighting factors. In some embodiments, a weighting factor of the second set of weighting factors may correspond to a data value in the region outside the k-space center of the first set of image data. In some embodiments, the sum of the number (or count) of the weighting factors of the first set and the number (or count) of the weighting factors of the second set may be the same as the number (or count) of the data points of the first set of image data. A data point of the first set of image data may correspond to one weighting factor, either from the first set of weighting factors or the second set of weighting factors.

As used herein, the first set of weighting factors (or the second set of weighting factors) corresponding to the first part (or the second part) may reflect the importance of the corresponding region (e.g., the region including the k-space center, the region outside the k-space center of the first set of image data) in the determination of a target image. In some embodiments, each weighting factor of the first set of weighting factors may be larger than each weighting factor of the second set of weighting factors. Accordingly, the region including the k-space center of the first set of image data may have a higher importance than the region outside the k-space center of the first set of image data in the determination of the target image. That is, data values with a relatively low frequency in the region including the k-space center of the first set of image data may have a higher importance than data values with a relatively high frequency in the region outside the k-space center of the first set of image data in the determination of the target image.

The first weight matrix corresponding to the first set of image data may be default settings of the data processing system 150 (or the image processing system 200) or may be adjustable under different situations. In some embodiments, each weighting factor of the first set of weighting factors (or the second set of weighting factors) may be the same as or be different from each other. For example, the first set of weighting factors may be set as 1, and the second set of weighting factors may be set as 0. That is, data values in the region including the k-space center of the first set of image data may remain unchanged (i.e., not changed in the weighted fusion process compared to their respective original values before the weighted fusion) when the weighted fusion is performed on the first set of image data and the second set of image data. As another example, the weighting factors in the first set of weighting factors may be in a range of, e.g., [0.8, 1.0], and the weighting factors in the second set of weighting factors may be in a range of, e.g., [0, 0.2]. That is, a changing extent of data values in the region including the k-space center of the first set of image data may be less than a changing extent of data values in the region outside the k-space center of the first set of image data when the weighted fusion is performed on the first set of image data and the second set of image data. In some embodiments, the weighting factors in the first weight matrix may be gradually decreased from the k-space center to the periphery of the k-space.

In 1802, the processing module 240 (e.g., the obtaining unit 1510) may obtain a second weight matrix corresponding to a second set of image data. In some embodiments, the size of the second weight matrix may be the same as the size of the second set of image data (or a second data array).

In some embodiments, the second weight matrix may include a third part and a fourth part. The third part may correspond to a region (e.g., the region 1002 or region 1003 illustrated in FIG. 10A) including the k-space center of the second set of image data. The third part may include a third set of weighting factors. In some embodiments, a weighting factor of the third set of weighting factors may correspond to a data value in the region including the k-space center of the second set of image data. The fourth part may correspond to a region (e.g., the region 1004 or the region 1001 illustrated in FIG. 10B) outside the k-space center of the second set of image data. The fourth part may include a fourth set of weighting factors. In some embodiments, a weighting factor of the fourth set of weighting factors may correspond to a data value in the region outside the k-space center of the second set of image data. In some embodiments, the sum of the number (or count) of the weighting factors of the third set and the number (or count) of the weighting factors of the fourth set may be the same as the number (or count) of the data points of the second set of image data. A data point of the second set of image data may correspond to one weighting factor, either from the third set of weighting factors or the fourth set of weighting factors.

As used herein, the third set of weighting factors (or the fourth set of weighting factors) corresponding to the third part (or the fourth part) may reflect the importance of the corresponding region (e.g., the region including the k-space center, the region outside the k-space center of the second set of image data) in the determination of a target image. In some embodiments, each weighting factor of the third set of weighting factors may be less than each weighting factor of the fourth set of weighting factors. Accordingly, the region outside the k-space center of the second set of image data may have a higher importance than the region including the k-space center of the second set of image data in the determination of the target image. That is, data values with a relatively high frequency in the region outside the k-space center of the second set of image data may have a higher importance than data values with a relatively low frequency in the region including the k-space center of the second set of image data in the determination of the target image.

The second weight matrix corresponding to the second set of image data may be default settings of the data processing system 150 or the image processing system 200 or may be adjustable under different situations. In some embodiments, each weighting factor of the third set of weighting factors (or the fourth set of weighting factors) may be the same as or be different from each other. For example, the third set of weighting factors may be set as 0, and the fourth set of weighting factors may be set as 1. That is, data values in the region outside the k-space center of the second set of image data may remain unchanged (i.e., not changed in the weighted fusion process compared to their respective original values before the weighted fusion) when the weighted fusion is performed on the first set of image data and the second set of image data. As another example, the weighting factors in the third set of weighting factors may be in a range of, e.g., [0, 0.2], and the weighting factors in the fourth set of weighting factors may be in a range of, e.g., [0.8, 1]. That is, a changing extent of data values in the region outside the k-space center of the second set of image data may be less than a changing extent of data values in the region including the k-space center of the second set of image data when the weighted fusion is performed on the first set of image data and the second set of image data. In some embodiments, the weighting factors in the second weight matrix may be gradually increased from the k-space center to the periphery of the k-space.

In some embodiments, each weighting factor of the third set of weighting factors may be less than each weighting factor of the first set of weighting factors. In some embodiments, each weighting factor of the fourth set of weighting factors may be larger than each weighting factor of the second set of weighting factors.

In some embodiments, the size of the first weight matrix may be the same as or be different from the size of the second weight matrix. One or more positions of the weighting factors in the first weight matrix may be consistent or inconsistent with one or more positions of the weighting factors in the second weight matrix.

In 1803, the processing module 240 (e.g., the processing unit 1520) may generate a target image by performing, according to the first weight matrix and the second weight matrix, a weighted sum of the first set of image data and the second set of image data in k-space. In some embodiments, the first set of image data may include a data array in k-space, and the first set of image data may be directly used in the weighted fusion operation. In some embodiments, the first set of image data may include a data array in an image domain, and the first set of image data may be transformed to k-space data by Fourier transform, and then the k-space data may be used in the weighted fusion operation. In some embodiments, the second set of image data may include a data array in k-space, and the second set of image data may be directly used in the weighted fusion operation. In some embodiments, the second set of image data may include a data array in an image domain, and the second set of image data may be transformed to k-space data by Fourier transform, and then the k-space data may be used in the weighted fusion operation.

In some embodiments, the data values in the region including the k-space center of the first set of image data or the second set of image data may determine an overall image contrast, brightness, and/or general shapes of organs of the subject in the first set of image data or the second set of image data. In some embodiments, the data values in the region outside the k-space center of the first set of image data or the second set of image data may determine the edges, details, and/or sharp transitions of the organs of the subject in the first set of image data or the second set of image data. Because the first set of image data are obtained based on k-space data generated by a magnetic resonance imaging (MRI) scanner (e.g., the MRI scanner 110), the overall image contrast, brightness, and/or general shapes of organs of the subject determined by the data values in the region including the k-space center of the first set of image data may have a relatively high quality. Because the second set of image data are generated by processing the first set of image data based on the first trained machine learning model, the edges, details, and/or sharp transitions of the organs of the subject determined by the data values in the region outside the k-space center of the second set of image data may have a relatively high quality. The weighted fusion operation may take full advantage of the data values in the region including the k-space center of the first set of image data and the data values in the region outside the k-space center of the second set of image data. Therefore, the target image generated based on the weighted fusion may have a relatively good overall image contrast, brightness, and/or general shapes of organs of the subject, and relatively clear edges, details, and/or sharp transitions of the organs of the subject.

In some embodiments, the processing module 240 may determine a target set of image data based on the first weight matrix, the second weight matrix, the first set of image data, and the second set of image data, according to Equation (10) as illustrated below:

$$K = K_1 \cdot W_1 + K_2 \cdot W_2, \tag{10}$$

where K refers to the target set (or array) of image data in k-space; $K_1$ refers to k-space data (array) corresponding to the first set of image data; $K_2$ refers to k-space data (array) corresponding to the second set of image data; $W_1$ refers to the first weight matrix corresponding to the first set of image data; and $W_2$ refers to the second weight matrix corresponding to the second set of image data. In some embodiments, a weighting factor of the first weight matrix associated with an element (x, y) in the first set of image data and a weighting factor of the second weight matrix associated with a corresponding element (x, y) in the second set of image data may satisfy Equation (11) as illustrated below:

$$W_1(x,y) + W_2(x,y) = 1, \tag{11}$$

where $W_1(x, y)$ refers to the weighting factor of the first weight matrix associated with the element (x, y) in the first set of image data; and $W_2(x, y)$ refers to the weighting factor of the second weight matrix associated with the corresponding element (x, y) in the second set of image data.

In some embodiments, the processing module 240 may determine the target image by perform an inverse Fourier transform on the target set of image data in k-space.

As described in the present disclosure, the first weight matrix corresponding to the first set of image data and the second weight matrix corresponding to the second set of image data may be generated according to a preset rule. The target image (e.g., an artifact-corrected MRI image) may be determined by performing a weighted fusion on the first set of image data and the second set of image data based on the first weight matrix and the second weight matrix. Accordingly, the first set of image data and the second set of image data may be combined more naturally. Therefore, the determined artifact-corrected MRI image may be more satisfactory for practical use.

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added elsewhere in the process 1800. For example, an operation for transforming the target set of image data to the target image may be added after operation 1803. As another example, if the size of the first weight matrix (or the first set of image data) is less than the size of the second weight matrix (or the second set of image data), then a padding operation (e.g., zero-padding) may be performed on the first weight matrix (and/or the first set of image data) before the weighted sum is performed.

Figure 19:
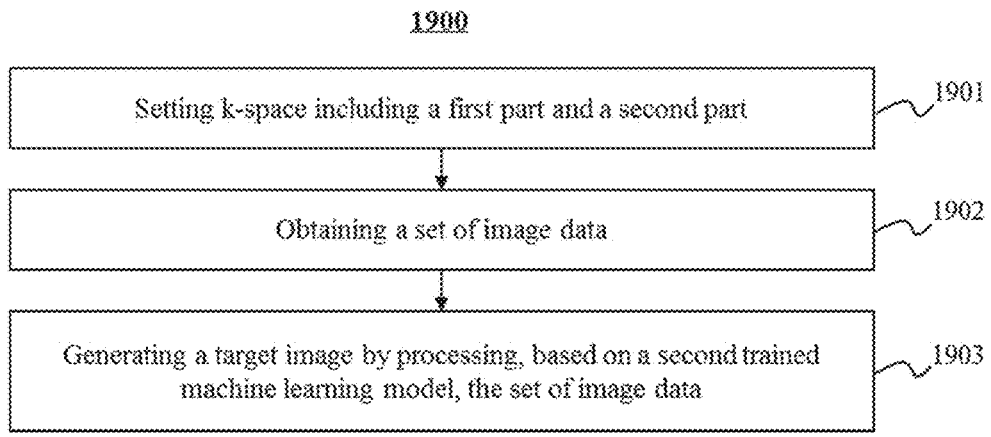
FIG. 19 is a flowchart illustrating an exemplary process for generating a target image according to some embodiments of the present disclosure.

FIG. 19 is a flowchart illustrating an exemplary process for generating a target image according to some embodiments of the present disclosure. The process 1900 may be executed by the data processing system 150 or the image processing system 200. For example, the process 1900 may be implemented as a set of instructions stored in the storage module 220. In some embodiments, one or more units in FIG. 15 may execute the set of instructions, and when executing the instructions, the unit(s) may be configured to perform the process 1900. The operations of the illustrated process presented below are intended to be illustrative. In some embodiments, the process 1900 may be accomplished with one or more additional operations not described and/or without one or more of the operations discussed. Additionally, the order in which the operations of the process 1900 illustrated in FIG. 19 and described below is not intended to be limiting.

In 1901, the processing module 240 (e.g., the setting unit 1540) may set k-space including a first part and a second part.

In some embodiments, the k-space may include the first part (e.g., region 1002 illustrated in FIG. 10A) and the second part (e.g., region 1001 illustrated in FIG. 10A). The first part may include the k-space center. In some embodiments, the first part may further include a first region (e.g., region 1004 illustrated in FIG. 10B) and a second region (e.g., region 1003 illustrated in FIG. 10B). The second region may include the k-space center.

In 1902, the processing module 240 (e.g., the obtaining unit 1510) may obtain a set of image data. In some embodiments, the set of image data may include a data array in k-space or a data array in an image domain.

In some embodiments, the processing module 240 may obtain the set of image data based on k-space data generated by an MRI scanner (e.g., the MRI scanner 110). For example, the processing module 240 may obtain the set of image data by performing an inverse Fourier transform on the k-space data generated by the MRI scanner. As another example, the processing module 240 may obtain the set of image data by collecting, using one or more reconstruction algorithms, the k-space data generated by the MRI scanner. The one or more image reconstruction algorithms may include a parallel imaging algorithm, a compressed sensing algorithm, a partial Fourier acquisition algorithm, a regridding algorithm, or the like, or any combination thereof.

In 1903, the processing module 240 (e.g., the processing unit 1520) may generate a target image by processing, based on a second trained machine learning model, the set of image data.

The second trained machine learning model may be configured to generate the target image with a relatively high resolution and/or a relatively low level of artifacts based on the set of image data with a relatively low resolution and/or a relatively high level of artifacts. In some embodiments, the second trained machine learning model may be configured to process the set of image data to a less extent in the first part than the second part. Accordingly, a changing extent of the set of image data in the first part may be less than a changing extent of the set of image data in the second part by the processing of the set of image data. For example, the second trained machine model may be configured to set a portion of the set of image data in the second region to be invariant during the processing.

In some embodiments, the second trained machine learning model may be generated by training a second preliminary machine learning model as described in connection with the training of the first machine learning model (e.g., FIG. 17, and descriptions thereof). The second preliminary machine learning model may be the same as or be different from the first preliminary machine learning model. For example, the processing module 240 may obtain a plurality of second sets of input image data. The processing module 240 may obtain a plurality of second sets of expected image data (e.g., one or more target images generated according to 1603 or 1803). The processing module 240 may train the second preliminary machine learning model based on the plurality of second sets of input image data and the plurality of second sets of expected image data. In some embodiments, the second preliminary machine learning model may be biased toward learning of characteristics of the plurality of second sets of expected image data in the second part with respect to the first part during the training process.

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added elsewhere in the process 1900. For example, an operation for preprocessing the set of image data may be added before operation 1903. Specifically, the processing module 420 may perform a low pass filtering on the set of image data.

FIG. 20 is a schematic diagram illustrating a machine learning model according to some embodiments of the present disclosure. In some embodiments, the machine learning model may be a neural network model. The machine learning model may be configured to determine a second set of image data with a relatively high resolution and/or a relatively low level of artifacts, based on a first set of image data with a relatively low resolution and/or a relatively high level of artifacts, as described elsewhere in the present disclosure (e.g., FIGS. 16, 17, and 19).

As illustrated in FIG. 20, the machine learning model may include an input layer 2320, an output layer 2360, and one or more hidden layers 2340 between the input layer 2320 and the output layer 2360. The hidden layers 2340 may include a convolution layer 2340-1, a pooling layer 2340-2, a fully connected layer 2340-N, or the like, or any combination thereof. The convolution layer 2340-1 may include a plurality of kernels (e.g., a kernel A, a kernel B, a kernel C, and a kernel D). As used herein, the kernel(s) may be used to extract features of the contrast information associated with an image (e.g., the first set of image data). In some embodiments, each of the plurality of kernels may extract features of high frequency component of the k-space of the first set of image data. The features of the high frequency component of the k-space may include coil combining coefficients, channel-related coefficients, convolution kernels, or the like.

The pooling layer 2340-2 may use output data from the convolution layer w340-1 as input data. The pooling layer 2340-2 may include a plurality of pooling nodes (e.g., a pooling node E, a pooling node F, a pooling node G, and a pooling node H). As used herein, the pooling node(s) may be used to sample the output data from the convolution layer 2340-1. Accordingly, the computational burden of the data processing system 150 or the image processing system 200 may be reduced, and the data processing speed may be increased. In some embodiments, the size of matrix associated with the high frequency component in the k-space corresponding to the pooling layer 2340-2 may be reduced.

The fully connected layer 2340-N may include a plurality of neurons (e.g., a neuron O, a neuron P, a neuron M, and a neuron N). Each of the plurality of neurons may be connected to one or more nodes in a previous layer (e.g., the pooling layer 2340-2). In the fully connected layer 2340-N, a plurality of vectors corresponding to the plurality of neurons may be determined based on the coil combining coefficients associated with the high frequency component in the k-space of the first set of image data. The plurality of vectors may be weighted based on a plurality of weighting coefficients.

In the output layer 2360, output data may be determined based on the plurality of vectors and the plurality of weighting coefficients obtained from the fully connected layer 2340-N. In some embodiments, the output data (e.g., the second set of image data) may include a data array in k-space or a data array in an image domain. The output data (e.g., the second set of image data) may have a relatively high resolution and/or a relatively low level of artifacts with respect to the corresponding input data (e.g., the first set of image data).

In some embodiments, the machine learning model may access a plurality of processors (e.g., a GPU) of the data processing system 150 or the image processing system 200. The plurality of processors may perform a parallel processing in one or more layers of the machine learning model. That is, the calculation burden of different nodes in one or more layers of, e.g., a CNN model, may be assigned to two or more processors. For example, one GPU may perform calculations corresponding to kernels A and B, and another GPU(s) may run calculations corresponding to kernels C and D in the convolution layer 2340-1. Similarly, calculations corresponding to different nodes in other types of layers in the CNN model may be performed in parallel by multiple GPUs.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the operator's computer, partly on the operator's computer, as a stand-alone software package, partly on the operator's computer and partly on a remote computer or entirely on the remote computer or server. In the latter scenario, the remote computer may be connected to the operator's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on a computing device including a storage device and at least one processor for image processing, the method comprising:

obtaining a first set of image data, the k-space of the first set of image data including a first part including the k-space central region and a second part outside of the first part;

generating a second set of image data by processing, based on a trained machine learning model, the first set of image data to a less extent in the first part than the second part so that a changing extent of the first set of image data in the first part is less than a changing extent of the first set of image data in the second part, wherein the second set of image data have a relatively high resolution and/or a relatively low level of artifacts with respect to the first set of image data; and generating a target image by performing a synthesis of the first set of image data and the second set of image data.

2. The method of claim 1, wherein the obtaining a first set of image data comprises:

obtaining the first set of image data based on k-space data generated by a magnetic resonance imaging (MRI) scanner.

3. The method of claim 2, wherein the obtaining the first set of image data based on k-space data generated by a magnetic resonance imaging (MRI) scanner comprises:

filling the first part of the k-space with k-space data generated by the MRI scanner; and padding the second part of the k-space with padded data.

4. The method of claim 2, wherein the obtaining the first set of image data based on k-space data generated by a magnetic resonance imaging (MRI) scanner comprises:

obtaining the first set of image data by performing an inverse Fourier transform on the k-space data generated by the MRI scanner.

5. The method of claim 2, wherein the obtaining the first set of image data based on k-space data generated by a magnetic resonance imaging (MRI) scanner comprises:

obtaining the first set of image data by collecting, using one or more reconstruction algorithms, the k-space data generated by the MRI scanner.

6. The method of claim 1, wherein the first set of image data includes a data array in k-space or a data array in an image domain.

7. The method of claim 1, wherein the second set of image data includes a data array in k-space or a data array in an image domain.

8. The method of claim 1, wherein the trained machine learning model is obtained according to a process, the process including:

obtaining a preliminary machine learning model;
obtaining a plurality of sets of input image data;
obtaining a plurality of sets of expected image data; and
obtaining the trained machine learning model by training, based on the plurality of sets of input image data and the plurality of sets of expected image data, the preliminary machine learning model.

9. The method of claim 8, wherein the plurality of sets of input image data include a plurality of data arrays in k-space or a plurality of data arrays in an image domain.

10. The method of claim 8, wherein the plurality of sets of expected image data include a plurality of data arrays in k-space or a plurality of data arrays in an image domain.

11. The method of claim 8, wherein each set of input image data of the plurality of sets of input image data corresponds to a set of expected image data of the plurality of sets of expected image data, and the each set of input image data have a relatively low resolution and/or a relatively high level of artifacts with respect to the corresponding set of expected image data.

12. The method of claim 11, wherein the obtaining a plurality of sets of input image data comprises:
obtaining a first set of input image data based on k-space data generated by a magnetic resonance imaging (MRI) scanner.

13. The method of claim 12, wherein the obtaining a plurality of sets of expected image data comprises:
reducing one or more artifacts in the first set of input image data by processing, based on one or more processing algorithms, the first set of input image data; and
designating the first set of processed input image data as a first set of expected image data corresponding to the first set of input image data.

14. The method of claim 11, wherein the obtaining a plurality of sets of expected image data comprises:
obtaining a second set of expected image data having a relatively high resolution and/or a relatively low level of artifacts by a magnetic resonance imaging (MRI) scanner.

15. The method of claim 11, wherein the obtaining a plurality of sets of expected image data comprises:
obtaining a second set of expected image data based on k-space data generated by a magnetic resonance imaging (MRI) scanner.

16. The method of claim 15, wherein the k-space of the second set of expected image data includes a first part including the k-space central region and a second part outside of the first part, the first part in the k-space of the second set of expected image data corresponds to the first part in the k-space of the input image data, and the second part in the k-space of the second set of expected image data corresponds to the second part in the k-space of the input image data.

17. The method of claim 1, wherein generating a target image by performing a synthesis of the first set of image data and the second set of image data comprises:
obtaining a first weight matrix corresponding to the first set of image data;
obtaining a second weight matrix corresponding to the second set of image data; and
generating the target image by performing, according to the first weight matrix and the second weight matrix, a weighted sum of the first set of image data and the second set of image data in k-space.

18. The method of claim 17, wherein
the first weight matrix includes a first part and a second part, the first part including the k-space central region, the first part including a first set of weighting factors, the second part including a second set of weighting factors, each of the first set of weighting factors being larger than each of the second set of weighting factors; and
the second weight matrix includes a third part and a fourth part, the third part including the k-space central region, the third part including a third set of weighting factors, the fourth part including a fourth set of weighting factors, each of the third set of weighting factors being smaller than each of the fourth set of weighting factors.

19. A method implemented on a computing device including a storage device and at least one processor for image processing, the method comprising:
setting k-space including a first part and a second part, the first part including the k-space central region, the second part being outside of the first part;
obtaining a set of image data; and
generating a target image by processing the set of image data based on a trained machine learning model;
wherein the trained machine learning model is configured to process the set of image data to a less extent in the first part than the second part so that a changing extent of the set of image data in the first part is less than a changing extent of the set of image data in the second part by the processing of the set of image data.

20. A system for image processing, comprising:
at least one storage device including a set of instructions or programs; and
at least one processor configured to communicate with the at least one storage device, wherein when executing the set of instructions or programs, the at least one processor is configured to cause the system to:
obtain a first set of image data, the k-space of the first set of image data including a first part including the k-space central region and a second part outside of the first part;
generate a second set of image data by processing, based on a trained machine learning model, the first set of image data to a less extent in the first part than the second part so that a changing extent of the first set of image data in the first part is less than a changing extent of the first set of image data in the second part, wherein the second set of image data have a relatively high resolution and/or a relatively low level of artifacts with respect to the first set of image data; and
generate a target image by performing a synthesis of the first set of image data and the second set of image data.

* * * * *